(12) United States Patent
Qin et al.

(10) Patent No.: US 8,389,728 B2
(45) Date of Patent: Mar. 5, 2013

(54) **POLLEN TUBE STIMULANTS FROM *ARABIDOPSIS* PISTILS**

(75) Inventors: Yuan Qin, Wuhan (CN); Ravishankar Palanivelu, Tucson, AZ (US); Ronald J. Wysocki, Jr., Tucson, AZ (US); Arpad Somogyi, Tucson, AZ (US); Yelena Feinstein, Tucson, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 327 days.

(21) Appl. No.: 12/732,938

(22) Filed: Mar. 26, 2010

(65) Prior Publication Data

US 2011/0111959 A1    May 12, 2011

Related U.S. Application Data

(60) Provisional application No. 61/280,664, filed on Nov. 6, 2009.

(51) Int. Cl.
*C07D 215/38* (2006.01)
(52) U.S. Cl. ..................................... 546/141; 546/153
(58) Field of Classification Search .................. 546/141, 546/153
See application file for complete search history.

(56) References Cited

U.S. PATENT DOCUMENTS

| 4,897,345 A | 1/1990 | Harris et al. |
| 6,303,587 B1 | 10/2001 | Yvin et al. |
| 2009/0181959 A1 | 7/2009 | Rodgers et al. |

OTHER PUBLICATIONS

Buchmann, CA 59:24754, abstract only of Wissenschaftliche Zeitschrift der Technischen Hochschule fuer Chemie "Carl Schorlemmer" Leuna-Merseburg, vol. 4, No. 3/4, pp. 219-225, 1962, abstract only.*
Burbulis et al., "A Null Mutation in the First Enzyme of Flavonoid Biosynthesis Does Not Affect Male Fertility in *Arabidopsis*," The Plant Cell, 8: 1013-1025 (1996).
Gilroy et al., "Signal processing and transduction in plant cells: the end of the beginning?" Nat Rev Mol Cell Biol, 2(4): 307-314 (2001).
Gu et al., "A Rho family GTPase controls actin dynamics and tip growth via two counteracting downstream pathways in pollen tubes," J Cell Biol, 169(1): 127-138 (2005).
Han et al., "Down-regulation of prostate specific antigen in LNCaP cells by flavonoids from the pollen of *Brassica napus L.*," Phytomedicine, 14(5): 338-343 (2007).
Higashiyama et al., "Guidance in vitro of the pollen tube to the naked embryo sac of *Torenia fournieri*," Plant Cell, 10(12): 2019-2032 (1998).
Higashiyama et al., "Pollen tube attraction by the synergid cell," Science, 293(5534): 1480-1483 (2001).
Johnson et al., "*Arabidopsis* hapless mutations define essential gametophytic functions," Genetics, 168(2): 971-982 (2004).
Kim et al., "Effects of flavonoids on pollen tube growth in *Arabidopsis thaliana*," J Plant Biol, 39: 273-278 (1996).
Lord et al., "The mechanisms of pollination and fertilization in plants," Ann Rev Cell Dev Biol, 18:81-105 (2002).
Lush, W.M. "Whither chemotropism and pollen tube guidance?," Trends Plant Sci, 4: 413-418 (1999).
Mo et al., "Biochemical complementation of chalcone synthase mutants defines a role for flavonols in functional pollen," Proc Natl Acad Sci U S A., 89(15): 7213-7217 (1992).
Palanivelu et al., "Pollen tube growth and guidance is regulated by POP2, an *Arabidopsis* gene that controls GABA levels," Cell, 114(1): 47-59 (2003).
Piggott et al., "Hydrolysis rates of alkyl and aryl sulfinamides: evidence of general acid catalysis," Tetrahedron Letters, 48: 7452-7455 (2007).
Prado et al., "Nitric oxide is involved in growth regulation and re-orientation of pollen tubes," Development, 131(11): 2707-2714 (2004).
Preuss et al., "A conditional sterile mutation eliminates surface components from *Arabidopsis* pollen and disrupts cell signaling during fertilization," Genes Dev, 7(6): 974-985 (1993).
Reger et al., "Chemotropic responses by pearl millet pollen tubes," Sexual Plant Reproduction, 5: 47-56 (1992).
Taylor et al., "Flavonoids as developmental regulators," Curr Opin Plant Biol, 8(3): 317-323 (2005).
Tsukamoto et al., "Studies on germination of chrysanthemum pollen II. Occurrence of a germination-promoting substance," Plant & Cell Physiol, 9: 237-245 (1967).
Weterings et al., "Experimental analysis of the fertilization process," Plant Cell, 16 (Suppl.): S107-118 (2004).
Wolters et al., "Lipids are required for directional pollen-tube growth," Nature, 392(6678): 818-821 (1998).
Ylstra et al., "Flavonols are *not* essential for fertilization in *Arabidopsis thaliana*," Plant Mol Biol, 32(6): 1155-1158 (1996).
Youn et al., "A simple and efficient preparation of sulfinyl chlorides from disulfides and sulfuryl chloride," Tetrahedron Letters, 27: 1493-1494 (1986).
Zheng et al., "The Rop GTPase switch turns on polar growth in pollen," Trends Plant Sci, 5(7):298-303 (2000).
Buchmann, "Chemical constitution and biological effect of methylquinolines," Wissenchaftliche Zeitschrift det Technischen Hochschule fuer Chemi "Carl Schorlemmer" Leuna-Merseburg, 4(3/4): 219-225 (Abstract only) (1962).
Vial et al., "*Burkholderia pseudomallei*, *B. thailandensis*, and *B. ambifaria* Produce 4-Hydroxy-2-Alkylquinoline Analogues with a Methyl Group at the 3 Position That Is Required for Quorum-Sensing Regulation," Journal of Bacteriology, 190(15):5339-5352 (2008).

* cited by examiner

*Primary Examiner* — D M Seaman
(74) *Attorney, Agent, or Firm* — Klarquist Sparkman, LLP

(57) ABSTRACT

This disclosure relates, inter alia, to stimulants of pollen tube germination and growth of pollen tubes, and methods of their use to stimulate in vitro and in vivo pollen germination and pollen tube growth.

8 Claims, 22 Drawing Sheets

Figure 1
A. Cut Pistil
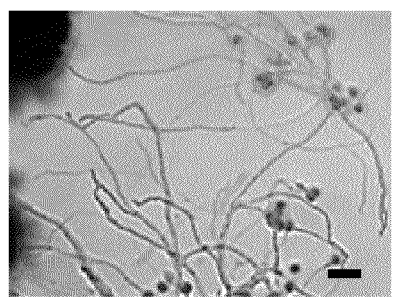
B. Cut Stem
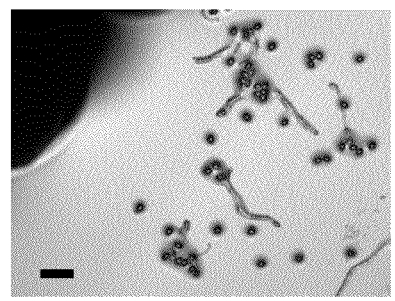
C. Ovule
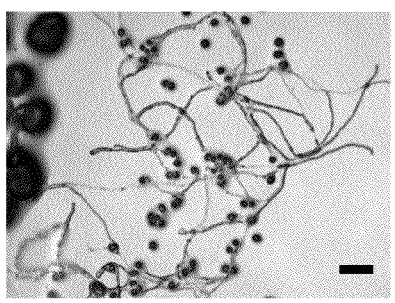
D. Leaf
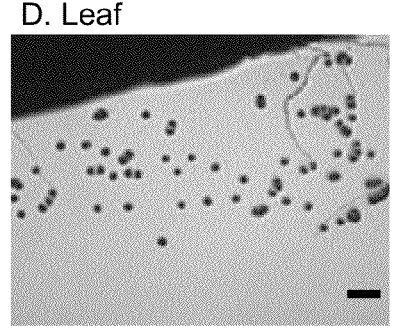
E. PGM
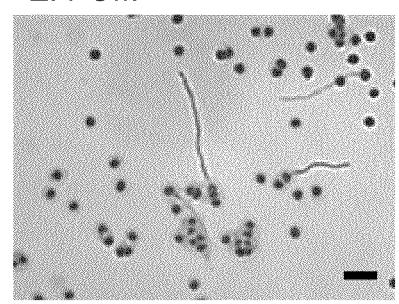
F. Cut Pistil Extract
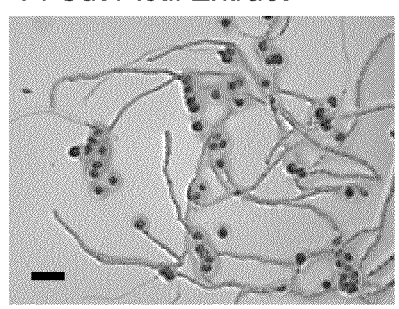
G. Ovule Extract
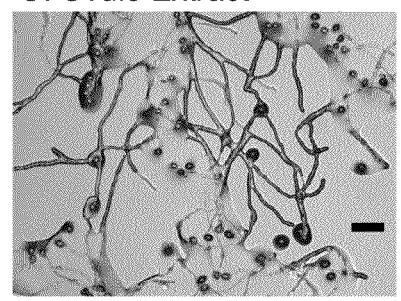
H. Pistil Extract
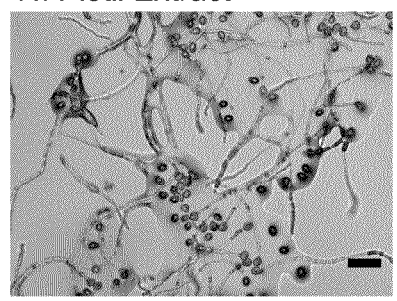

Figure 2 (cont)
C
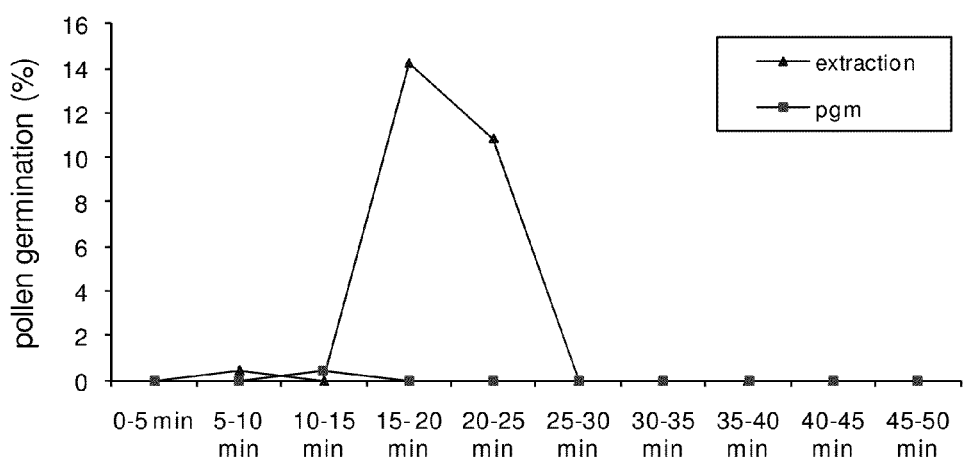
D
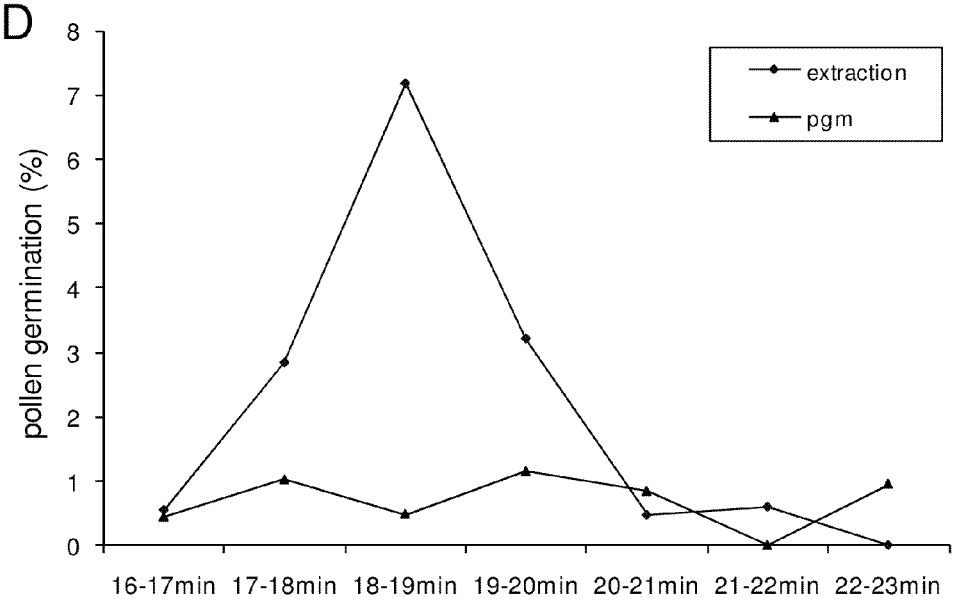

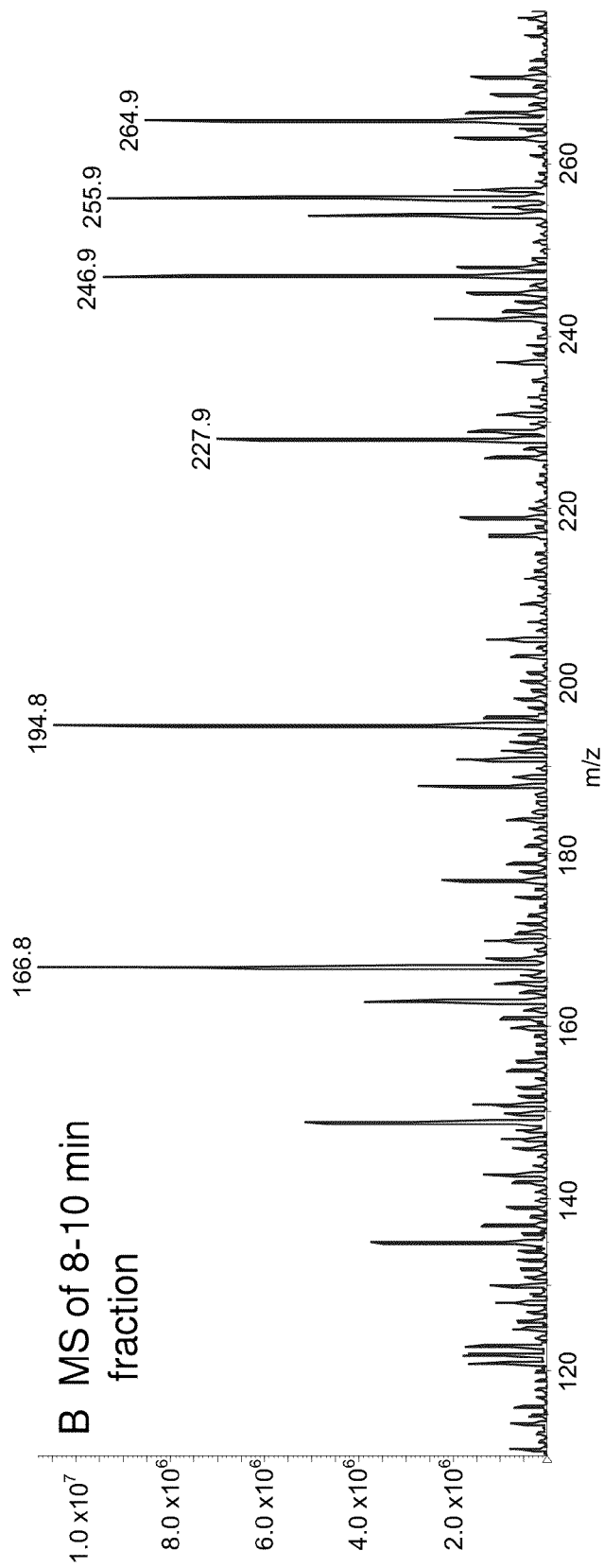
Figure 3 (Cont.) B MS of 8-10 min fraction

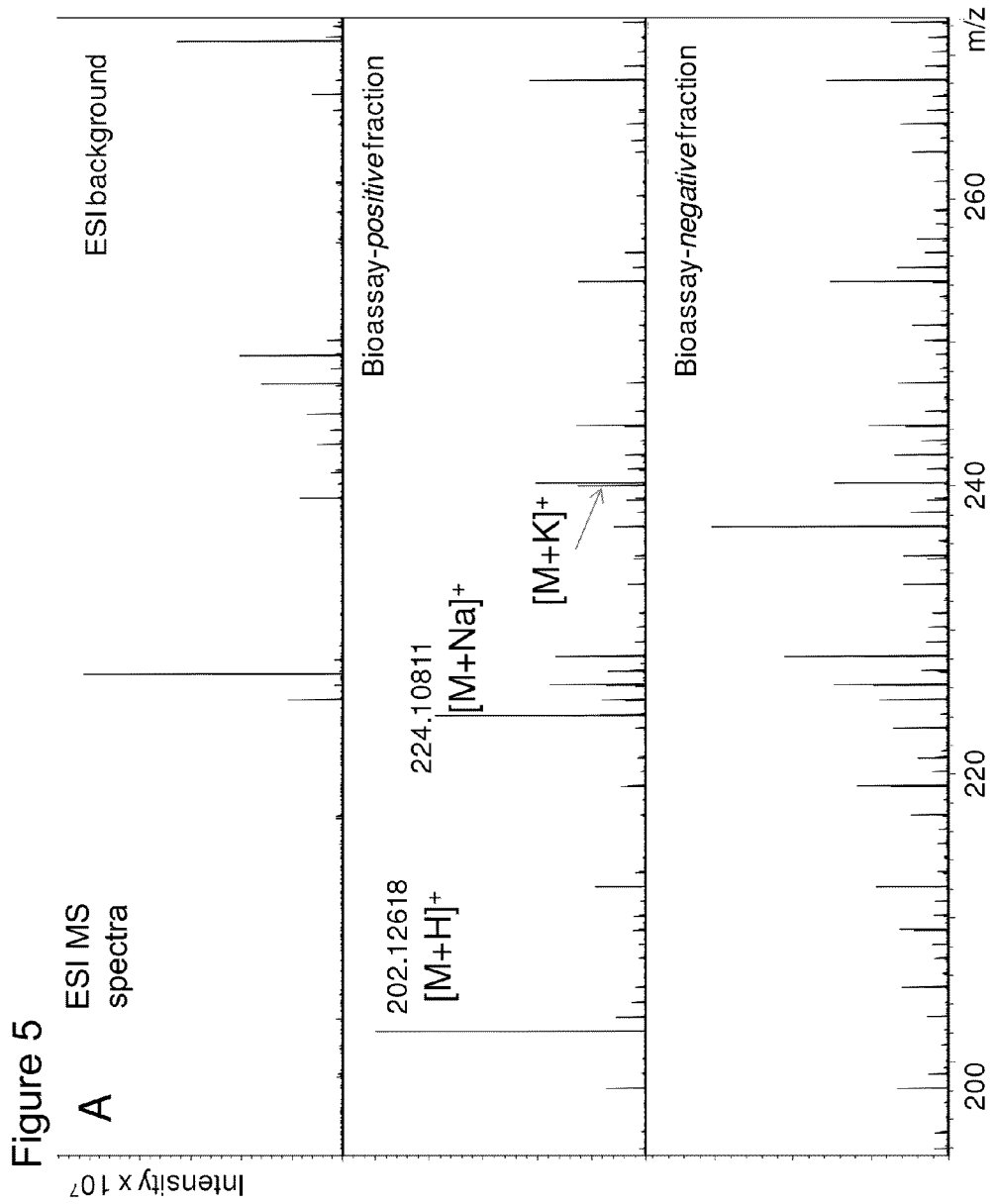

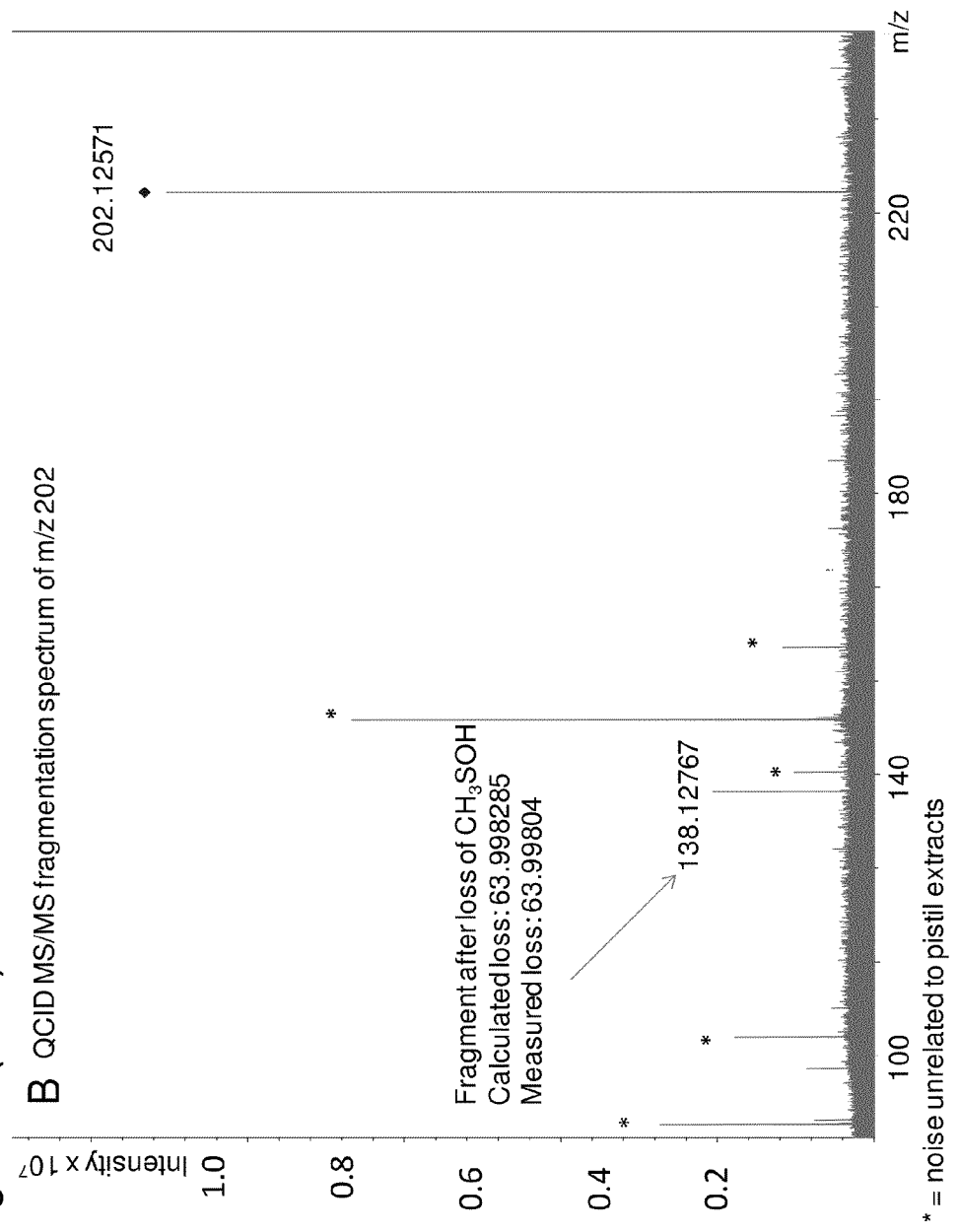

Figure 10
A
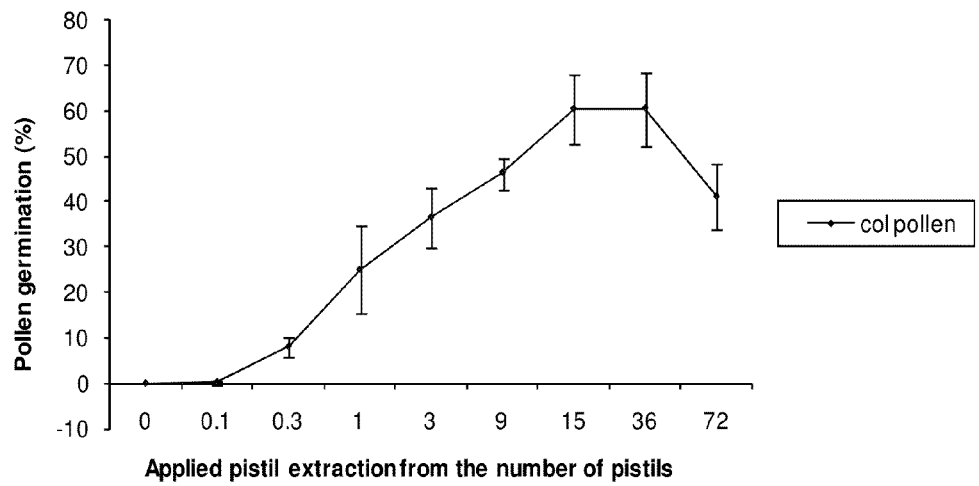
B
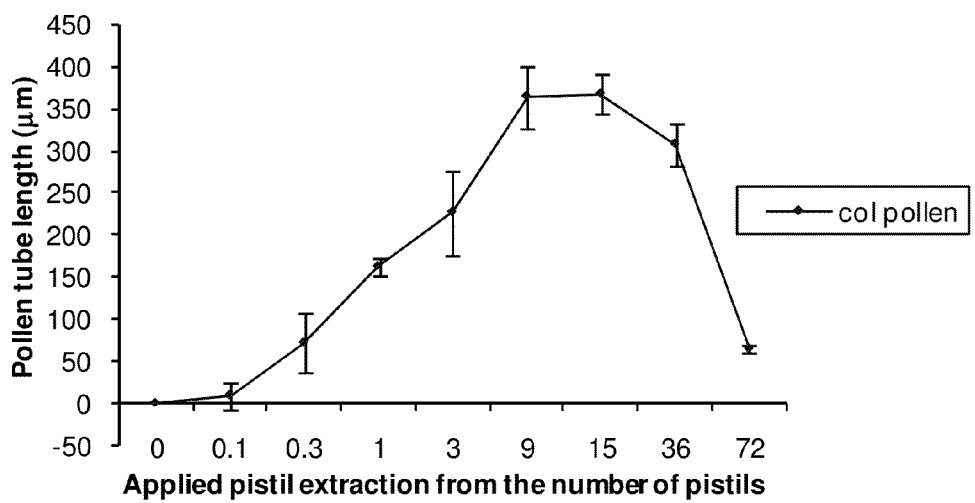

Figure 10 (cont)
C
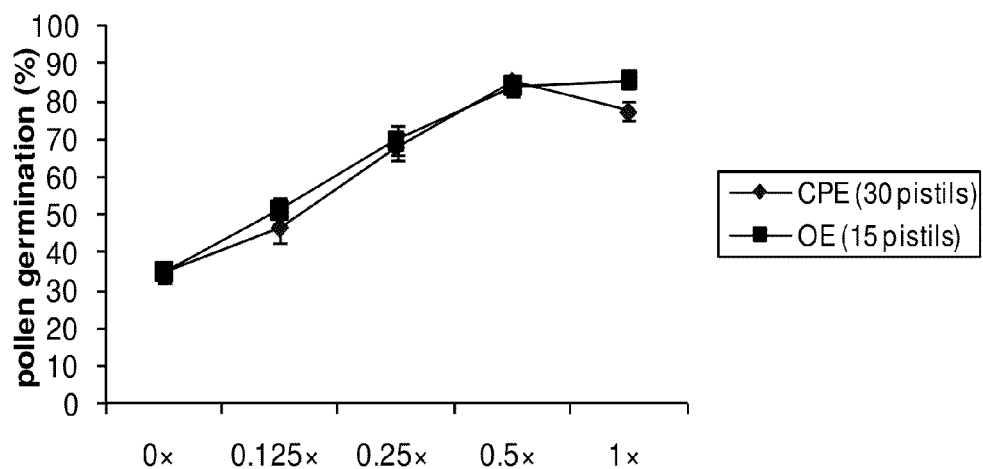
D
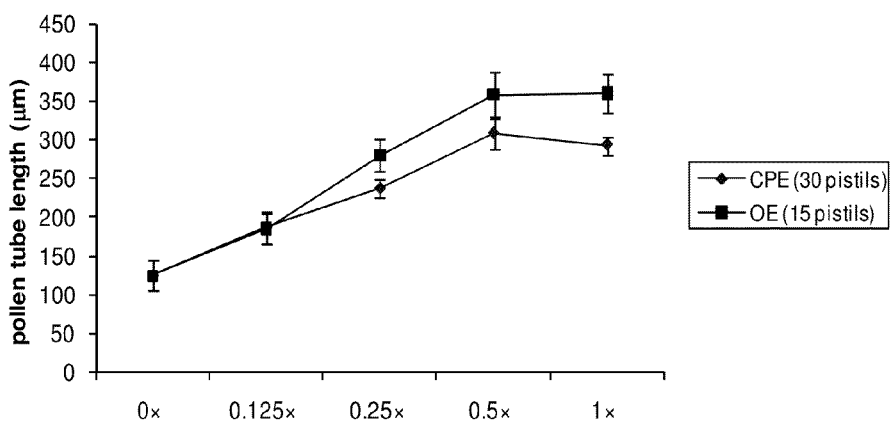

Figure 10 (cont)
E
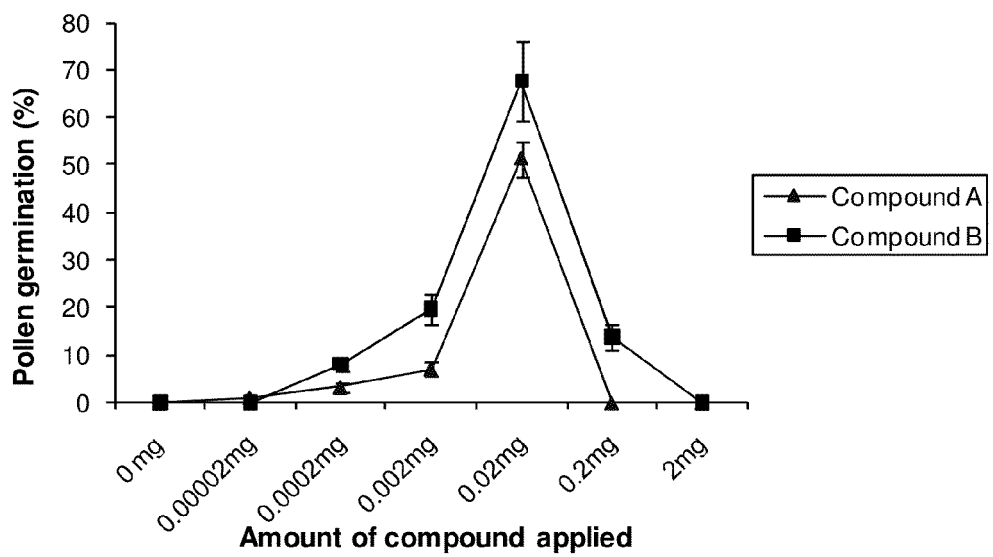
F
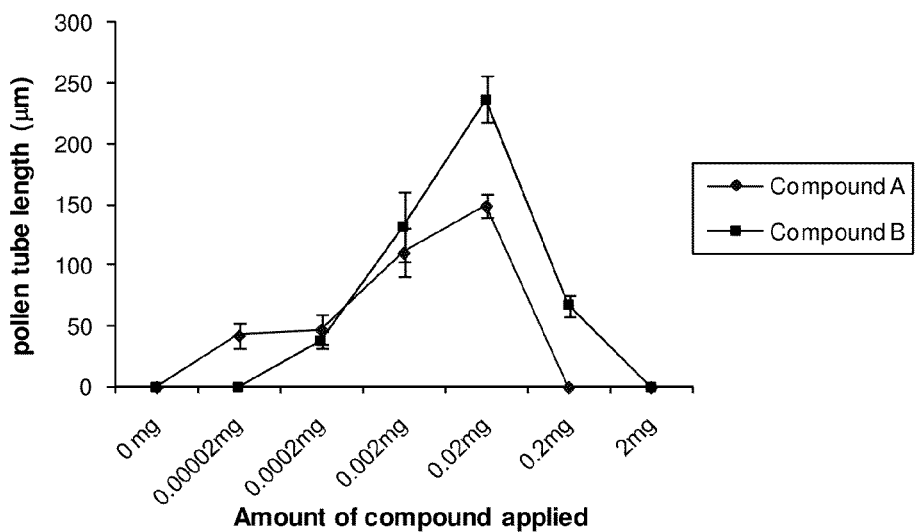

Figure 10 (cont)
G
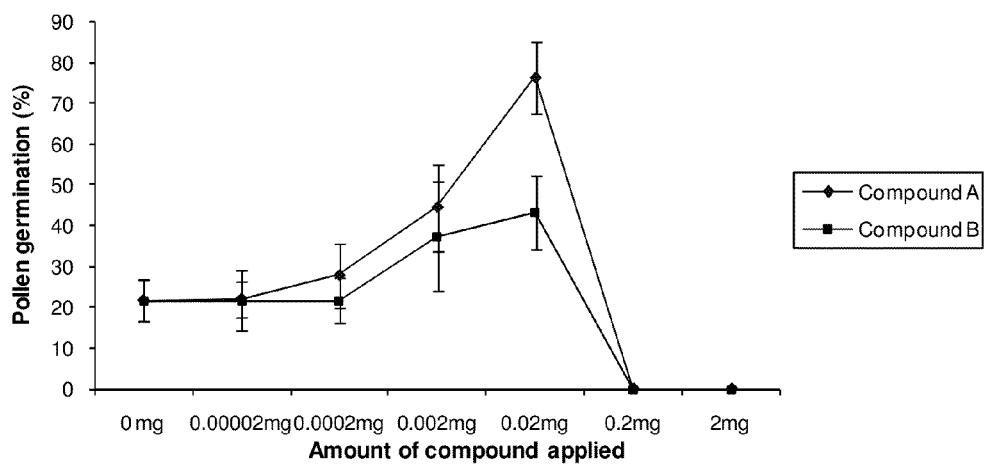
H
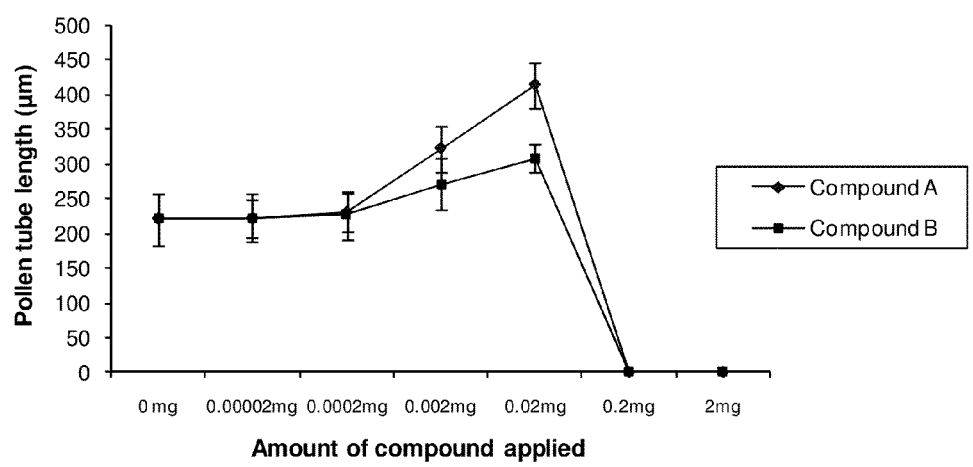

Figure 11
A
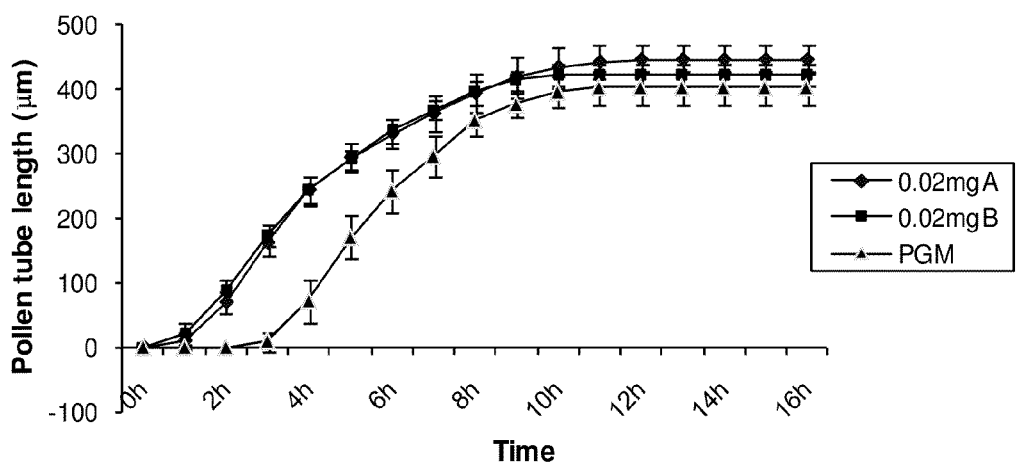
B
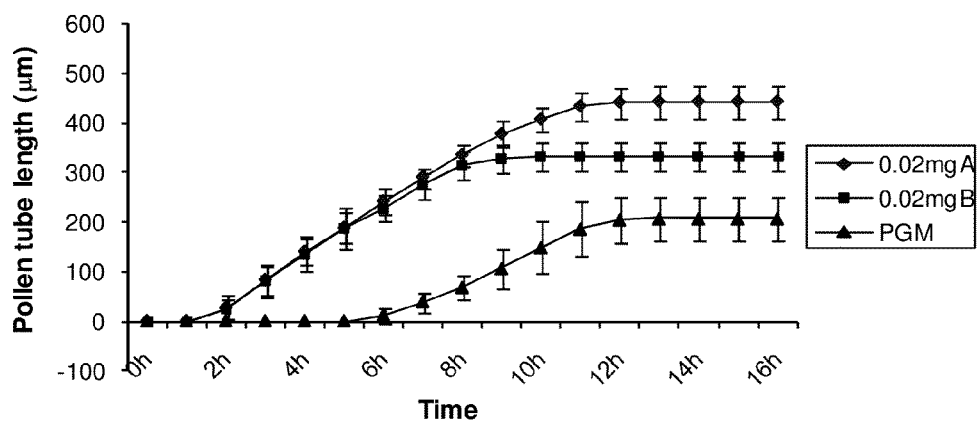

POLLEN TUBE STIMULANTS FROM *ARABIDOPSIS* PISTILS

CROSS REFERENCE TO RELATED APPLICATION

This application claims priority to and the benefit of U.S. Provisional Application No. 61/280,664 filed Nov. 6, 2009, which is incorporated by reference herein in its entirety.

ACKNOWLEDGMENT OF GOVERNMENT SUPPORT

This invention was made in part with government support under National Science Foundation research grant IOS 0723421. The government has certain rights in the invention.

FIELD

This disclosure relates, inter alia, to stimulants of pollen tube germination and growth of pollen tubes, and methods of their use to stimulate in vitro and in vivo pollen germination and pollen tube growth.

BACKGROUND

During flowering plant reproduction, pollen lands on the surface of the pistil, extends a tube that carries sperm to an ovule and effects fertilization. Pistil cells are critical for inducing pollen germination and tube growth, yet only a few of these signals have been identified. After a pollen grain lands on the surface of a pistil, it absorbs water from the stigma, forms a pollen tube and transports all cellular contents along with both sperm cells to its tip (Weterings and Russell, *Plant Cell*, 16 (Suppl):S107-118, 2004). Pollen tubes invade the pistil and migrate past several different cell types, growing between the walls of the stigma cells, traveling through the extracellular matrix of the transmitting tissue, and finally arriving at the ovary, where they migrate up the funiculus, and enter the micropyle to fertilize an egg and a central cell (Lord and Russell, *Ann. Rev. Cell Dev. Biol.*, 18:81-105, 2002). Typically, only one pollen tube enters the ovule through the micropyle, terminates its journey within a synergid cell, and bursts to release the two sperm cells, of which one will fuse with the egg cell to generate an embryo and the second one fuses with the central cell to form an endosperm.

A combination of genetic, biochemical and in vitro assays have defined signals that contribute to the early stages of pollen tube guidance. The early phase of pollen tube growth—germination and penetration of the stigma—is influenced by the stigma exudate in plants with wet stigmas (e.g. tobacco) and by the pollen coat in species with dry stigmas (e.g. *Arabidopsis*). Lipids in the exudate and the pollen coat are required for pollen germination (Preuss et al., *Genes Dev*, 7:974-985, 1993; and Wolters-Arts et al., *Nature*, 392:818-821, 1998), perhaps functioning by controlling the flow of water to pollen (Lush, *Trends Plant Sci*, 4:413-418, 1999).

Besides genetic analyses, in vitro growth assays have been used to characterize pollen tube behavior. Such assays were used to investigate intracellular responses within pollen tubes. For example, cues such as a $Ca^{2+}$ gradient at the tip of pollen tubes were shown to be critical for their growth. Disrupting this gradient by iontophoretic microinjection or by incubation with $Ca^{2+}$ channel blockers can change the direction of tube growth (Gilroy and Trewavas, *Nat Rev Mol Cell Biol*, 2:307-314, 2001). The $Ca^{2+}$ gradient in pollen tubes is controlled by Rho GTPases; injection of antibodies against these proteins into pollen tubes or expression of dominant-negative forms of Rho GTPase causes the tip-focused $Ca^{2+}$ gradient to diffuse and eliminates tube growth (Zheng and Yang, *Trends Plant Sci*, 5:298-303, 2000), presumably by disrupting F-actin assembly (Gu et al., *J Cell Biol*, 169:127-138, 2005).

In vitro-grown pollen tubes also respond to extracellular growth and guidance cues. Lily pollen tubes are attracted to chemocyanin and repelled by a point source of nitric oxide, NO (Prado et al., *Development*, 131:2707-2714, 2004). In addition, in vitro grown pearl millet pollen tubes are attracted to ovary extracts (Reger et al., *Sexual Plant Reproduction*, 5:47-56, 1992). In *Torenia fournieri*, pollen tube guidance across a simple medium and into the ovule was achieved only after pollen tubes were grown through a stigma and style (Higashiyama et al., *Plant Cell*, 10:2019-2032, 1998). In this species, the female gametophyte protrudes from the ovule, and pollen tubes enter the micropyle without interacting with a funiculus (Id.). Using this system, it was demonstrated that when synergid cells were ablated, pollen tubes did not penetrate the micropyle, demonstrating that the synergid is the source of the attractant that facilitates pollen tube entry into the micropyle (Higashiyama et al., *Science*, 293:1480-1483, 2001).

*Chrysanthemum* in vitro pollen germination was notably increased in the presence of floral organs and although the factor responsible was not identified, it was found to be soluble in water, ether or methanol (Tsukamoto and Matsubara, *Plant & Cell Physiol.*, 9:237-245, 1967). From *Petunia* stigma extracts, kaempferol was isolated and showed to stimulate pollen germination (Mo et al., *PNAS*, 89:7213-7217, 1992). Consistent with these observations, loss of maize and *Petunia* chalcone synthase (chs), the first enzyme of flavonoid biosynthesis, resulted in white pollen that was incapable of germinating, growing and fertilizing ovules (Id.). Notwithstanding these observations concerning the role of flavonoids in pollen function, null mutation in the single chalcone synthase gene in *Arabidopsis* did not affect pollen germination, growth or its ability to fertilize ovules (Burbulis et al., *Plant Cell*, 8:1013-1025, 1996). *Arabidopsis thaliana* is arguably the most widely used plant model organism to study plant biology. Thus, a continuing need exists to identify the factors responsible for stimulation of pollen tube germination and growth.

SUMMARY

Described herein are isolated stimulants of pollen tube germination and pollen tube growth, and formulations thereof, comprising a compound of Formula I:

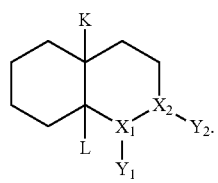

In this formula, $X_1$ is C or N. If $X_1$ is C, then $X_2$ is N; $Y_1$ is H, lower alkyl, alkyl, or substituted alkyl; and $Y_2$ is

wherein R is H, lower alkyl, alkyl, or substituted alkyl. If $X_1$ is N, then $X_2$ is C; $Y_1$ is

wherein R is H, lower alkyl, alkyl, or substituted alkyl; and $Y_2$ is H, lower alkyl, alkyl, or substituted alkyl. One or both K and L are H, lower alkyl, alkyl, or substituted alkyl.

Also described are methods of stimulating pollen tube germination and pollen tube growth by exposure of pollen to an effective amount of an isolated pollen growth stimulant comprising at least one compound of Formula I and allowing the pollen sufficient time to germinate and grow a pollen tube. Such stimulation can be in vitro or in vivo.

Methods of rendering pollen capable of stimulated germination and pollen tube growth are also described, comprising exposing pollen to an effective amount of an isolated pollen growth stimulant comprising at least one compound of Formula I.

The foregoing and other objects, features, and advantages of the invention will become more apparent from the following detailed description, which proceeds with reference to the accompanying figures.

ABBREVIATIONS

CPE cut pistil exudates
DP declustering potential
ESI electrospray ionization
FT-ICR fourier-transform ion cyclotron resonance
GCMS gas chromatography/mass spectroscopy
HPLC high pressure liquid chromatography
LC-MS liquid chromatography-mass spectroscopy
MS/MS tandem mass spectroscopy
NMR nuclear magnetic resonance
OE ovule exudates
PGM pollen growth medium

BRIEF DESCRIPTION OF THE FIGURES

FIG. 1 is a series of photomicrographs showing the results of pollen exposed to various stimuli in an in vitro pollen germination assay. *Arabidopsis* pollen was germinated on plates containing solid PGM and various stimuli. FIG. 1A shows the effect of cut pistils; FIG. 1B shows the effect of cut stems; FIG. 1C shows the effect of ovules; FIG. 1D shows the effect of leaf; FIG. 1E shows the effect of PGM; FIG. 1F shows the effect of cut pistil extract; FIG. 1G shows the effect of ovule extract; and FIG. 1H shows the effect of pistil extract. The black bar in each figure represents 50 micrometers.

FIG. 5A shows FT-ICR spectra of bioassay positive (middle) and negative (bottom) CPE fractions.

FIG. 5B is a MS/MS fragmentation spectrum of the m/z 202 ion. Starred peaks indicate noise unrelated to pistil extracts. Diamond indicates the m/z 202 ion.

FIG. 10 is a series of line graphs showing the concentration-dependent stimulation of *Arabidopsis* pollen in the in vitro growth assay by pistil extracts, ovule extracts, Compound A, and Compound B.

FIGS. 10A and 10B are line graphs showing the effect of CPE produced from increasing numbers of pistils on *Arabidopsis* Columbia pollen germination % and pollen tube length as measured after overnight incubation.

FIGS. 10C and 10D are line graphs showing the effect of increasing concentrations of CPE or OE on germination % and pollen tube length of *Arabidopsis* Columbia pollen as measured after overnight incubation.

FIGS. 10E and 10F are line graphs showing the effect of increasing concentrations of Compound A or Compound B on germination % and pollen tube length of *Arabidopsis* Columbia pollen as measured after a three-hour incubation.

FIGS. 10G and 10H are line graphs showing the effect of increasing concentrations of Compound A or Compound B on germination % and pollen tube length of *Arabidopsis* Landsberg pollen as measured after overnight incubation.

FIG. 11A is a line graph comparing rate of *Arabidopsis* Columbia pollen tube growth in the presence of 0.02 mg Compound A, 0.02 mg Compound B, and PGM.

FIG. 11B is a line graph comparing rate of *Arabidopsis* Landsberg pollen tube growth in the presence of 0.02 mg Compound A, 0.02 mg Compound B, and PGM.

DETAILED DESCRIPTION

I. Terms

Figure 2:
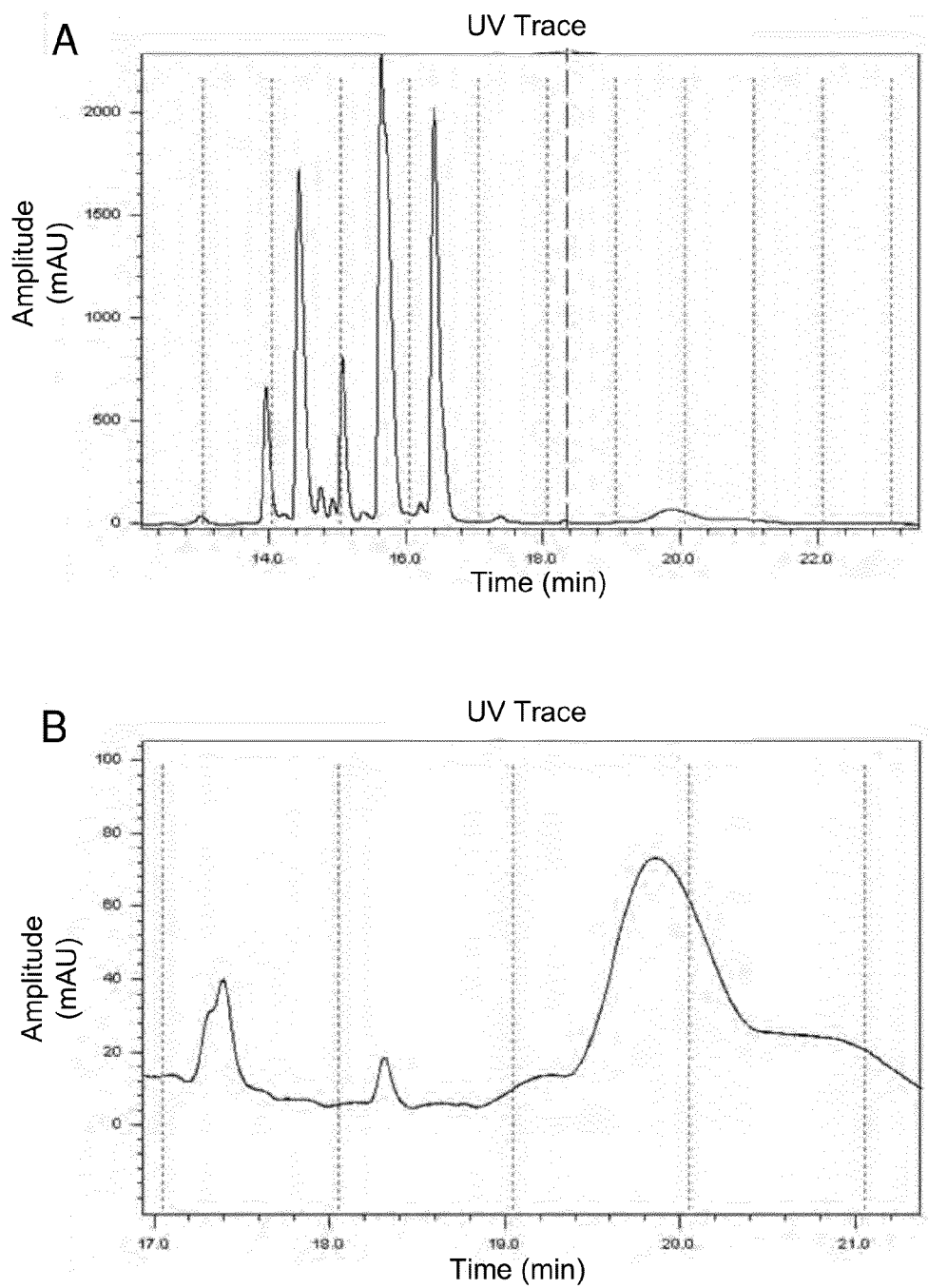
FIGS. 2A and 2B show the reverse phase C18 column chromatography fractionation spectra of CPE.
FIGS. 2C and 2D are respective graphs showing the in vitro assay of the CPE chromatography fractions for pollen-stimulating activity.

Unless otherwise noted, technical terms are used according to conventional usage. In order to facilitate review of the various embodiments of this disclosure, the following explanations of specific terms are provided:

Adjuvant: A chemical added to a pollen growth stimulant formulation or tank mix to improve mixing and application or enhance performance, including wetting agents and spreaders. Common adjuvants include, but are not limited to, wetting agents, such as anionic, cationic, nonionic, and amphoteric surfactants, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, herbicides, antibiotics, fungicides, nematicides, or pesticides.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A lower alkyl group is a saturated branched or unbranched hydrocarbon having from 1 to 10 carbon atoms. Preferred alkyl groups have 1 to 4 carbon atoms. Alkyl groups may be substituted alkyls wherein one or more hydrogen atoms are substituted with a substituent such as halogen, cycloalkyl, alkoxy, amino, hydroxyl, aryl, or carboxyl.

Antioxidant: An adjuvant, such as vitamin E, vitamin C, or beta carotene that protects a compound, for example a pollen growth stimulant, from the damaging effects of oxidation.

Buffer: An ionic compound that resists changes in its pH.

Derivative: A compound or portion of a compound that is derived from or is theoretically derivable from a parent compound.

Drift Control Agent: An adjuvant used to reduce the fine particles in the spray pattern that are responsible pollen growth stimulant drift.

Extender: An adjuvant added to a pollen growth stimulant to modify, dilute, or adulterate it.

Extract: A concentrated preparation of a composition, such as a pollen growth stimulant, obtained by removing the active constituents of the composition with suitable solvents, optionally evaporating all or nearly all of the solvent, and adjusting the residual mass or powder to the a pre-determined standard amount. An extract is "enriched" for a product, such as a pollen growth stimulant, if the activity or amount of a component of interest is increased substantially in the extract as compared to other extracts or to the same amount of the extracted original composition.

Exudate: A preparation of a composition from a natural source, such as plant pistil tissue, obtained by incubating the natural source in a suitable buffer or solvent and allowing the composition to enter the buffer or solvent by passive diffusion.

Foaming agent: An adjuvant used to reduce foaming in a spray system so that pumps and nozzles can operate properly.

Effective amount: An amount of a specific compound, or a derivative or modification thereof, that has the desired biological effect of the compound. In particular examples, the compound is a pollen growth stimulant. An effective amount of a pollen growth stimulant may be an amount sufficient to stimulate the germination and growth of pollen tubes from at least some of the pollen exposed to the stimulant. An effective amount may also be an amount sufficient to render pollen capable of exhibiting stimulated germination and growth of pollen tubes under conducive environmental conditions. In specific embodiments of the disclosure, an effective amount of pollen growth stimulant promotes (stimulates) pollen germination and pollen tube growth in at least 10% of the pollen treated. In particular embodiments of the disclosure, an effective amount of a pollen growth stimulant (or a related compound) stimulates pollen germination and pollen tube growth in at least 20%, at least 30%, at least 40%, or even 50% or more, of a pollen population. In more particular embodiments of the disclosure, an effective amount of a pollen growth stimulant stimulates pollen germination and pollen tube growth in over 80%, 90%, or nearly 100% of a pollen population.

Isolated: An isolated biological agent or component has been substantially separated, produced apart from, or purified away from other biological agents or components in the environment or from a cell of the organism in which the agent or component naturally occurs. In some examples, an isolated biological agent or component is a small molecule that has been isolated and purified by passive diffusion of the small molecule or by standard extraction and purification methods. The term also embraces biological agents or components prepared by recombinant expression in a host cell as well as those that have been chemically synthesized extrabiologically. The term isolated does not require absolute purity; rather, this is intended as a relative term. Thus, for example, an isolated pollen growth stimulant is one in which the pollen growth stimulant is more enriched than in its natural environment within a cell. In some examples, an isolated preparation is purified such that the pollen growth stimulant is at least 50% of the total biochemical content of the preparation.

Pollen: A naturally produced material (usually granular or particulate in nature) containing the male gametes of seed plants. Upon transfer of pollen from the anther of a flower of a plant to the stigma at the top of the pistil of the same or different flower, pollen germinates, growing a pollen tube that enters the stigma, travels through the style, and delivers sperm to the ovule.

Pollen growth stimulant: A pistil-produced compound capable of stimulating the germination of pollen and the growth of a pollen tube.

Preservative: An adjuvant that inhibits degradation of a pollen growth stimulant formulation.

Purified: The term purified does not require absolute purity; rather, it is intended as a relative term. Thus, for example, a purified small molecule preparation is one in which the small molecule referred to is more pure than in its natural environment within a cell.

Soluble powder: A pollen growth stimulant formulation that, when mixed with water or other non-organic solvent, dissolves readily and forms a true solution. Soluble powder formulations are dry and include the active ingredient and additives. When thoroughly mixed, no further agitation is necessary to keep the active ingredient dissolved in solution.

Solution: A liquid formulation that includes an active ingredient and an additive. Solution formulations are designed for those active ingredients that dissolve readily in water or other non-organic solvent.

Solvent: A substance (usually liquid) suitable for, or employed in solution, or in dissolving something.

Spreader: An adjuvant that allows a pollen growth stimulant to form a uniform coating layer over the treated surface.

Stabilizer: A substance that renders or maintains a solution, mixture, suspension, or state resistant to chemical change.

Surfactant: A type of adjuvant designed to improve the dispersing/emulsifying, absorbing, spreading, sticking and/or pest-penetrating properties of a formulation for application on a plant. Surfactants can be divided into the following five groupings: 1) non-ionic surfactants, 2) crop oil concentrates, 3) nitrogen-surfactant blends, 4) esterified seed oils, and 5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate.

Cationic surfactants include quaternary ammonium salts carrying, as N-substituents, an 8 to 22 carbon straight or branched chain alkyl radical. The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Thickener: An adjuvant that reduces drift by increasing droplet size and reducing volume of spray contained in drift-prone droplets.

Timed-Release Coating: A coating on or in a solid or particulate formulation that retards degradation and prolongs pollen growth stimulant activity. Coatings can be divided into three categories: (1) coatings that directly degrade in the presence of water, (2) coatings that are broken apart by wet and dry cycles, and (3) coatings degraded by specific temperatures, for example Degree Herbicide® by Monsanto.

Water-Resistant Coating: A coating on or in a solid or particulate pollen growth stimulant formulation that repels water and delays dissolution of the pollen growth stimulant.

Wettable powder: A dry, finely ground formulation in which the active ingredient is combined with a finely ground carrier (usually mineral clay), along with other ingredients to enhance the ability of the powder to suspend in water or other non-organic solvent. Wettable powders are one of the most widely used plant treatment formulations and offer low cost and ease of storage, transport, and handling; lower phytotoxicity potential than emulsifiable concentrates and other liquid formulations; and less skin and eye absorption hazard than emulsifiable concentrates and other liquid formulations. Some disadvantages are that they require constant and thorough agitation in the spray tank, are abrasive to pumps and nozzles (causing premature wear), may produce visible residues on plant and soil surfaces, and can create an inhalation hazard to the applicator while handling (pouring and mixing) the concentrated powder. Typical solid diluents are described in Watkins et al., *Handbook of Insecticide Dust Diluents and Carriers,* 2nd Ed., Dorland Books, Caldwell, N.J. The more absorptive diluents are preferred for wettable powders and the denser ones for dusts.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

II. Overview of Several Embodiments

Provided herein are isolated pollen growth stimulants, comprising a compound of Formula I:

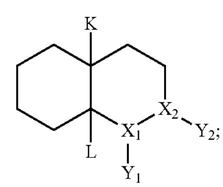

wherein $X_1$ is C or N. If $X_1$ is C, then $X_2$ is N; $Y_1$ is H, lower alkyl, alkyl, or substituted alkyl; and $Y_2$ is wherein R is H, lower alkyl, alkyl, or substituted alkyl. If $X_1$ is N, then $X_2$ is C; $Y_1$ is wherein R is H, lower alkyl, alkyl, or substituted alkyl; and $Y_2$ is H, lower alkyl, alkyl, or substituted alkyl. One or both K and L are H, lower alkyl, alkyl, or substituted alkyl.

In particular embodiments, the isolated pollen growth stimulant is a composition of Formula II or Formula III; wherein Formula II is:

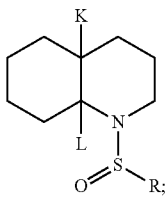

wherein one or more of K, L, and R is H, alkyl, lower alkyl, or substituted alkyl; and
wherein Formula III is:

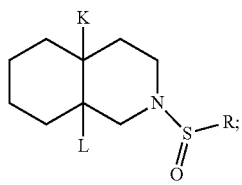

wherein one or more of K, L, and R is H, alkyl, lower alkyl, or substituted alkyl.

In particular examples, the isolated pollen growth stimulant is Compound A or Compound B; wherein Compound A is:

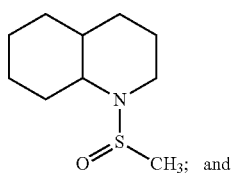

wherein Compound B is:

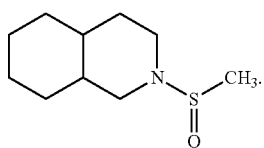 [SMILES: CS(=O)N1CCC2CCCCC2C1]

In further examples, the isolated pollen growth stimulant is provided as part of a formulation, comprising the isolated pollen growth stimulant and at least one of a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, or a pesticide. In other examples, the formulation further comprising pollen. In still other examples, the pollen is from a plant of family Brassicaceae, such as a plant selected from the group consisting of a species of *Arabidopsis, Olimarabidopsis, Capsella, Sisimbrium*, and *Brassica*.

Also provided herein are compositions, comprising the described isolated pollen growth stimulants and pollen. In particular examples, the pollen is from a plant of family Brassicaceae, such as a plant selected from the group consisting of a species of *Arabidopsis, Olimarabidopsis, Capsella, Sisimbrium*, and *Brassica*.

Additionally provided are methods of stimulating pollen germination and pollen tube growth comprising exposing pollen to an effective amount of at least one isolated pollen growth stimulant comprising a compound of Formula I:

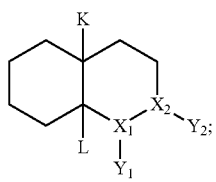

wherein $X_1$ is C or N. If $X_1$ is C, then $X_2$ is N; $Y_1$ is H, lower alkyl, alkyl, or substituted alkyl; and $Y_2$ is

wherein R is H, lower alkyl, alkyl, or substituted alkyl. If $X_1$ is N, then $X_2$ is C; $Y_1$ is

wherein R is H, lower alkyl, alkyl, or substituted alkyl; and $Y_2$ is H, lower alkyl, alkyl, or substituted alkyl. One or both K and L are H, lower alkyl, alkyl, or substituted alkyl. Sufficient time is allowed for the pollen to germinate and grow a pollen tube, thereby stimulating pollen germination and pollen tube growth.

In particular examples, the pollen is exposed to at least one isolated pollen growth stimulant having a formula of Formula II or Formula III;
wherein Formula II is:

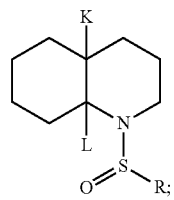

wherein one or more of K, L, and R is H, alkyl, lower alkyl, or substituted alkyl; and wherein Formula III is:

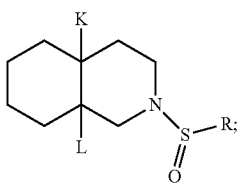

wherein one or more of K, L, and R is H, alkyl, lower alkyl, or substituted alkyl.

In other examples, the pollen is exposed to at least one isolated pollen growth stimulant having a formula of Compound A or Compound B;
wherein Compound A is:

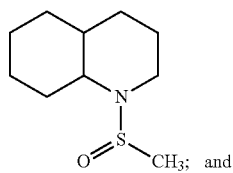 [SMILES: CS(=O)N1CCCC2CCCCC21 ; "and"]

wherein Compound B is:

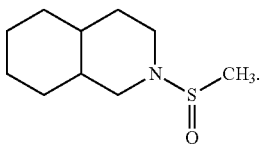 [SMILES: CS(=O)N1CCC2CCCCC2C1]

In particular examples of the methods of stimulating pollen germination and pollen tube growth, the at least one isolated pollen growth stimulant is a component of a pistil extract or exudate. In other examples, the at least one isolated pollen growth stimulant is synthesized extrabiologically. In some examples, exposing the pollen to the at least one isolated pollen growth stimulant comprises placing the pollen in or on pollen growth medium in vitro. In other examples, the at least one isolated pollen growth stimulant is added to the pollen growth medium either prior or after to placing the pollen in or on the medium. In some examples of in vitro pollen stimulation, the at least one isolated pollen growth stimulant is a component of a pistil extract or exudate. In other examples, it is synthesized extrabiologically.

In further examples of in vitro stimulation, the at least one isolated pollen growth stimulant significantly increases the percentage of germinated pollen in comparison to the percentage of pollen not exposed to the pollen growth stimulant. In yet further examples, the at least one isolated pollen growth stimulant significantly increases pollen tube length in comparison to pollen tube length of pollen not exposed to the pollen growth stimulant. In particular examples, the pollen is from a plant of family Brassicaceae, such as a plant selected from the group consisting of a species of *Arabidopsis, Olimarabidopsis, Capsella, Sisimbrium*, and *Brassica*. In yet other examples, the at least one isolated pollen growth stimulant is a component of a formulation also comprising a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, or a pesticide.

In some embodiments of the methods of stimulating pollen germination and pollen tube growth, exposing the pollen to the at least one isolated pollen growth stimulant includes placing the pollen on the stigma of a plant in vivo. In particular examples, the plant is a member of family Brassicaceae, such as a plant selected from the group consisting of a species of *Arabidopsis, Olimarabidopsis, Capsella, Sisimbrium*, and *Brassica*. In some examples, the plant is a mutant plant that is unable to produce or respond to the at least one isolated pollen growth stimulant. In further examples, the at least one isolated pollen growth stimulant significantly increases percentage of germinated pollen in comparison to percentage of germinated pollen not exposed to the pollen growth stimulant, which can be indicated by an increased fruit or seed yield from the plant grown either in optimal temperature or at higher or lower than optimal temperature (such as heat or cold stress).

In yet further examples, in vivo exposure of the pollen to the at least one isolated pollen growth stimulant further comprises applying the at least one isolated pollen growth stimulant to the plant in a formulation that also comprises a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, or a pesticide.

Also provided are methods of rendering pollen capable of exhibiting stimulated germination and pollen tube growth, comprising exposing pollen to an effective amount of at least one of the described isolated pollen growth stimulants. In particular examples, the at least one isolated pollen growth stimulant is a component of a formulation further comprising a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, or a pesticide.

III. Isolated Pollen Growth Stimulants

Described herein are isolated pollen growth stimulants that are capable of increasing pollen tube germination and pollen tube growth. The isolated pollen growth stimulants are composed of compounds having a structure of Formula I:

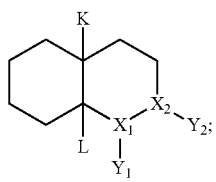

wherein $X_1$ is C or N. If $X_1$ is C, then $X_2$ is N; $Y_1$ is H, lower alkyl, alkyl, or substituted alkyl; and $Y_2$ is

wherein R is H, lower alkyl, alkyl, or substituted alkyl. If $X_1$ is N, then $X_2$ is C; $Y_1$ is

wherein R is H, lower alkyl, alkyl, or substituted alkyl; and $Y_2$ is H, lower alkyl, alkyl, or substituted alkyl. One or both K and L are H, lower alkyl, alkyl, or substituted alkyl.

In particular examples, the isolated pollen growth stimulants are compounds of Formula II or Formula III, wherein Formula II is:

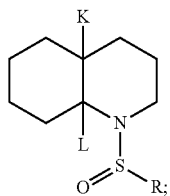

and wherein Formula III is:

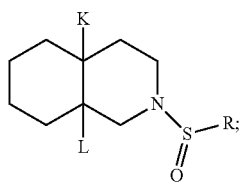

wherein one or more of K, L, and R is H, alkyl, lower alkyl, or substituted alkyl.

One of skill in the art will recognize that compounds having a structure of Formulae II, and III are equivalent to optical isomers thereof. With reference to Formulae II and III, such optical isomers can have a sulfinylated nitrogen in place of any of the unlabeled saturated carbon atoms of the quinoline rings (except for those bonded to K and L).

In particular embodiments, a pollen growth stimulant of Formulae I-III has a chemical formula of $C_{10}H_{20}NSO$. In particular examples, the isolated pollen growth stimulant corresponds to a compound having the structure of 1-methylsulfinyldecahydroquinoline, or derivatives thereof, also referred to herein as Compound A, wherein the structure of Compound A is:

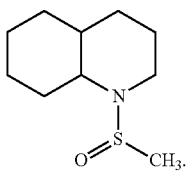

In other examples, the isolated pollen growth stimulant corresponds to a compound having the structure of 2-methylsulfinyldecahydroisoquinoline, or derivatives thereof, which is also referred to herein as Compound B, and wherein the structure of Compound B is:

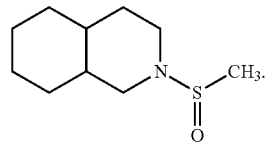 [SMILES: CS(=O)N1CCC2CCCCC2C1]

In particular embodiments, the isolated pollen growth stimulants described herein can be one or more biologically active components of an extract or exudate that is produced from pistil tissue of a plant. In some examples, the extract or exudate is produced from one or more of the stigma, style, or ovary of a flower. Any method that enables the release of small, organic-insoluble and aqueous or alcohol-soluble molecules can be used to produce an extract or exudate containing one or more of the described pollen growth stimulants. For example, the pistil tissue can be ground up and extracted with an organic solvent, such as ethyl acetate and the like, wherein the insoluble fraction contains a pollen growth stimulant-containing extract. In other examples, a pollen growth stimulant-containing exudate can be produced by incubation of cut pistil tissue in an aqueous or alcohol-containing solvent for any length of time sufficient to allow the diffusion of pollen growth stimulant into the solvent. In particular examples, one or more pollen growth stimulants can be further purified from stimulant-containing extracts or exudates by standard chromatographic techniques known to the art.

In other embodiments, the isolated pollen growth stimulants described herein and produced extrabiologically by standard methods of chemical synthesis known to the art (for example in Trost and Fleming (eds.), *Comprehensive Organic Synthesis*, Oxford, N.Y.: Pergamon, 1991; and Barton, *Comprehensive Organic Chemistry: The Synthesis and Reactions of Organic Compounds*. Oxford: Pergamon, 1979). Other exemplary methods of extrabiological synthesis of each of the described pollen growth stimulants are described in Example 4.

The pollen growth stimulants described herein are poorly soluble to insoluble in non-alcoholic organic solvents such as ethyl acetate and the like, and are relatively soluble in aqueous solvents, for example, pollen growth medium, or alcohol-based organic solvents such as methanol and the like. This insolubility in ethyl acetate is in contrast to the flavonoid-type pollen growth stimulants of, for example, maize and *Petunia* which are soluble in ethyl acetate (Mo et al., *PNAS*, 89:7213-7217, 1992). Additionally, the pollen growth stimulants described herein are biologically active up to the boiling point of water (100° C.). The pollen growth stimulants described herein also remain biologically active under acidic and basic conditions, such as from a pH of 2 to 12.

IV. Chemical Formulations

In some embodiments, the pollen growth stimulating compounds of the present disclosure can be combined with appropriate solvents or surfactants to form a product called a formulation. Formulations enable the uniform distribution of a relatively small amount of the pollen growth stimulating compounds over a comparatively large area, such as multiple plants growing in a particular plant. In addition to providing the user with a form of a pollen growth stimulating compound that is easy to handle, formulating the compound can enhance its stimulating effects, improve its ability to be applied to a plant, enable the combination of aqueous-soluble and organic-soluble compounds, improve its shelf-life, and protect it from adverse environmental conditions while in storage or transit.

The primary kinds of formulations are: solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Solution formulations are designed for those active ingredients that dissolve readily in water or other non-organic solvents such as methanol. The formulation is a liquid and consists of the active ingredient and additives. Suitable liquid carriers, such as solvents, may be organic or inorganic. Water is one example of an inorganic liquid carrier. Although the pollen growth stimulants describe herein are insoluble in most organic solvents, formulations may contain one or more components that are soluble in an organic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Typical liquid diluents and solvents are described in Marsden, *Solvents Guide,* 2nd Ed., Interscience, NY, 1950. Solubility under 0.1% is preferred for suspension concentrates; solution concentrates are preferably stable against phase separation at 0° C. *McCutcheon's Detergents and Emulsifiers Annual*, Allured Publ. Corp., Ridgewood, N.J., as well as Sisely and Wood, *Encyclopedia of Surface Active Agents*, Chemical Publ., Co., Inc., NY 1964, list surfactants and recommended uses.

Soluble powder formulations are similar to solutions in that, when mixed with water, they dissolve readily and form a true solution. Soluble powder formulations are dry and include the active ingredient and additives. When thoroughly mixed, no further agitation is necessary to keep the active ingredient dissolved in solution.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., *Handbook of Insecticide Dust Diluents and Carriers,* 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications. In some embodiments of the disclosure, the percentage by weight of the active ingredient will be from about 0.1% to about 90%. Higher concentrations are usually employed for commercial purposes or products during manufacture, shipment, or storage; such embodiments have concentrations at least about 10%, or from about 25% to about 90% by weight. Prior to use, a highly concentrated formulation may be diluted to a concentration appropriate for the intended use, such as from about 0.1% to 10%, or from about 1% to 5%.

In some embodiments of the disclosure, inactive ingredients (that is, adjuvants) are added to pollen growth stimulant formulations to improve the performance of the formulation. For example, in one embodiment of the disclosure, a pollen growth stimulant is formulated with a surfactant. A surfactant (surface active agent) is a type of adjuvant formulated to improve the dispersing/emulsifying, absorbing, spreading, and sticking properties of the spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides. Such carriers and additives may be used in solid, liquid, gas, or gel form, depending on the embodiment and its intended application.

In particular examples, the pollen growth stimulant formulations are in a dried form and are mixed with pollen. Such mixtures render the exposed pollen capable of exhibiting stimulated germination and pollen tube growth under the proper germination conditions, such as in conditions sufficient to dissolve the pollen growth stimulant.

V. Methods of Stimulating Pollen Growth

Pollen, such as that of *Arabidopsis thaliana*, will germinate in vitro and produce pollen tubes in pollen growth medium (PGM) without additional stimulating factors (see FIG. 1, for example). However, the rate of such in vitro germination is slow, and overall yield of germination under such conditions is quite low. With the isolation of the pollen growth stimulants provided herein, methods of rendering pollen capable of exhibiting stimulated germination, and methods of stimulating pollen germination and pollen tube growth will be apparent to one of skill in the art.

As described herein, mixing pollen with an effective amount of at least one of the isolated pollen growth stimulating compounds described herein will produce a composition that is then capable of exhibiting stimulated pollen germination and pollen tube growth. Such germination and pollen tube growth can be induced under conditions that are suitably conducive to pollen germination, for example sufficiently moist, nutritive, or warm conditions.

Also as described herein, pollen germination and pollen tube growth are stimulated by exposing pollen to an effective amount of at least one of the isolated pollen growth stimulating compounds described above and allowing sufficient time for pollen germination and pollen tube growth. In particular embodiments, the isolated pollen growth stimulant is at least one compound of Formula I, Formula II, or Formula III. In some examples, the pollen growth stimulant is a compound of Formula II with a chemical formula of $C_{10}H_{20}NSO$ and having the structure of 1-methylsulfinyldecahydroquinoline (Compound A), or a derivative thereof. In other examples, the pollen growth stimulant is a compound of Formula III with a chemical formula of $C_{10}H_{20}NSO$ and having the structure of 2-methylsulfinyldecahydroisoquinoline (Compound B) or a derivative thereof.

The isolated pollen growth stimulant can be isolated from a biological source, such as pistil tissue of a plant. When isolated from plant pistils, the pollen growth stimulant can be isolated from one or more of the stigma, style, or ovary of the pistil. In some examples, the pollen growth stimulant is isolated from pistil tissue as a component of an extract or exudate. In other examples, the pollen growth stimulant is further purified from pistil extracts or exudates by standard biochemical purification methods known to the art, for example liquid chromatography and the like. In other examples, the pollen growth stimulant is produced extrabiologically by chemical synthesis techniques known to the art, such as those described in Example 4.

The amount of time sufficient to allow for pollen germination and pollen tube growth following exposure to a pollen growth stimulant will vary by largely pollen type and by concentration of isolated pollen growth stimulant used. In some examples, it is necessary to allow one or several hours such as 2, 3, 4, 5, 6 or more hours for pollen germination and pollen tube growth. In other examples it is necessary to allow great time, such as 10, 11, 12 or more hours for pollen germination and pollen tube growth.

In particular examples, exposure of pollen to the pollen growth stimulants described herein results in a significant increase in the percentage of germinating pollen (pollen that has initiated pollen tube growth) in comparison to pollen that is not exposed to the pollen growth stimulant. In some examples, in increase in percentage up to 5%, up to 10%, up to 20%, up to 30%, up to 50%, up to 60%, up to 70%, up to 80%, or up to 90% or more of germinating pollen is achieved in comparison to pollen not exposed to a pollen growth stimulant. Stimulation of pollen germination can be determined in vitro by visual inspection of pollen placed on solid or in liquid pollen growth medium, or by any other method known to the art of determining pollen germination. In vivo, stimulation of pollen germination can be determined by any method that either directly documents pollen tube growth in chemically fixed pistils or indirectly indicates stimulated pollen tube growth through increased yield of a fertilized plant, for example, increased seed or fruit yield in comparison to plants not exposed to the pollen growth stimulant (for example, see Palanivelu et al., *Cell,* 114:47-59, 2003; and Johnson et al., *Genetics,* 168:971-982, 2004).

Similarly, exposure of pollen to an effective amount of one or more of the isolated pollen growth stimulants, or functional derivative thereof, described herein will result in a significant increase in pollen tube length from the exposed pollen in comparison to pollen that is not stimulant-exposed. In some examples, an increase pollen tube length up to 5%, up to 10%, up to 20%, up to 30%, up to 50%, up to 60%, up to 70%, up to 80%, up to 90% is achieved in comparison to the length of pollen tubes from pollen not exposed to a pollen growth stimulant.

The pollen growth stimulants described herein were identified from *Arabidopsis thaliana*, but one of skill in the art will understand that pollen from a range of plants can be stimulated by the described pollen stimulants. Thus, in some examples, the pollen that is exposed to one or more of the pollen growth stimulants can be pollen from any strain/ecotype of *Arabidopsis thaliana*, or from other species of the same family as that of *Arabidopsis thaliana* (Brassicaceae), such as species of *Olimarabidopsis, Capsella, Sisimbrium,* and *Brassica*. In particular examples, the pollen is from plants of *Brassica oleraceae*, such as cabbage, broccoli, cauliflower, kale, kohlrabi and the like. Pollen from any plant that is sufficiently evolutionarily related to *Arabidopsis* can be used in the methods described herein.

In some embodiments, the pollen is germinated in vitro on solid or in liquid medium. The medium can be any type known to the art capable of supporting pollen germination and pollen tube growth. In some examples where pollen is germinated on solid media, the pollen growth stimulant is applied to the media prior to placement of the pollen on the media. In other examples the pollen growth stimulant is applied after the pollen is placed on the medium Likewise, in those examples where the pollen is germinated in liquid media, the pollen growth stimulant can be applied to the media before or after placement of the pollen in the media.

In other embodiments, the pollen is germinated in vivo on a plant. The plant can be any species of plant sufficiently related to *Arabidopsis* to be stimulated by the pollen growth stimulants described herein, such as plants from family of Brassicaceae. In particular examples, the plant is any species or ecotype of *Arabidopsis*. In other examples, the plant is a species of *Olimarabidopsis, Capsella, Sisimbrium,* and *Brassica*. In particular examples, the plant is a *Brassica oleraceae*, such as cabbage, broccoli, cauliflower, kale, kohlrabi and the like. In some examples, the plant is wild type for the ability to produce the applied pollen growth stimulant. In those examples, exposure of the pollen growth stimulant can increase germination yield, but it can also synchronize seed or fruit production, as the plants will be simultaneously exposed to a pollen germination and pollen tube growth initiation signal.

In other examples, the plant is a mutant plant that is either unable to produce or respond to the pollen growth stimulant. In such examples, the plant is conditionally sterile and will only be fertile upon exposure to the pollen growth stimulant. In such examples, exposure to pollen germination and pollen tube growth will synchronize fertilization of the plant and seed and fruit production.

As described above, the effective amount of the pollen growth stimulant can be mixed in a formulation that can enhance transport, stability, and application of the pollen growth stimulant. Such formulations can then be used in the methods described herein of stimulating pollen germination and pollen tube growth.

The following examples are provided to illustrate certain particular features and/or embodiments. These examples should not be construed to limit the invention to the particular features or embodiments described.

EXAMPLES

Example 1

Diffusible Pistil Factors Induce Pollen Germination and Pollen Tube Growth

This example shows the detection of a diffusible pistil factor that is capable of stimulating pollen germination and pollen tube growth.

Methods

Pollen Germination Medium (PGM):

PGM was prepared according to the protocol of the Zhengbio Yang laboratory, University of California, Riverside. PGM is composed of: 18% sucrose, 0.01% boric acid, 1 mM $CaCl_2$, 1 mM $Ca(NO_3)_2$, and 1 mM $MgSO_4$. The medium is adjusted to pH 7.0 before use. Solid medium for pollen germination and pollen tube growth is produced by addition of 0.5% Noble agar (Difco) to liquid PGM.

Cut Pistil Exudates Preparation:

For CPE collection, fifteen surgically removed unpollenated cut pistils (stigma and style portion) were placed vertically, with the cut end immersed in 50 μL of liquid pollen growth medium in a depression slide. The cut pistils were incubated in the buffer for 12 hours in a humid chamber at room temperature (~24° C.). The liquid medium containing the secretions was separated from the tissues and was either immediately used to measure germination and growth activity or stored at −20° C.

Pollen Tube Germination and Growth Assays:

Assays were performed on sold PGM. Cut pistils (stigma and style portion of pistil) were placed on solid PGM cut-end down. Pollen was placed on PGM near pistils and observed as described below. For evaluating germination and growth activities of CPE, liquid CPE was dispensed into a hole cut in the solid PGM, and allowed it to diffuse into the surrounding solid medium. This arrangement reduced the amount of CPE required for each experiment. Pollen was placed within a 2 mm radius from the hole in which CPE was dispensed. After 16 hours, ImageJ image analysis software (available on-line at http://rsb.info.nih.gov/ij/download.html) was used to quantify germination and growth of pollen tubes.

Results

The effects of one or more diffusible factors from the pistil on pollen germination and pollen tube growth were studied using an in vitro pollen growth assay. Pollen placed near a cut pistil (stigma and style portion of a pistil), germinated nearly 2.5 fold better than the pollen placed on growth medium devoid of any pistil (99% germination with pistil (FIG. 1A) compared to 42% without a pistil (FIG. 1E); 9 assays; Table 1, below). In addition, pollen tubes proximal to a pistil grew nearly 3 times longer than those that were grown without a pistil (382.80 μm long near a pistil (FIG. 1A) compared to 147.78 μm on growth medium without a pistil (FIG. 1E); 9 assays; Table 2). Pollen tube germination and growth inducing activity is pistil-specific, as cut inflorescence stems (FIG. 1B) did not induce pollen germination and growth under similar conditions (64% germination and 183.15 μm tube length; values that are indistinguishable from those that were grown without any pistil or in the presence of leaf extracts; Tables 1 and 2, below and FIG. 1D). These results suggested that physical interaction between pollen tubes and pistil tissues is not a prerequisite for pollen tube stimulation and that capacitance factors are diffusible.

The observation that pollen tube capacitance factors are secreted from the cut pistil tissues also suggested that growth stimulation activity will be present in the cut pistil exudates (CPEs). CPEs are less complex and separate the capacitance activity away from other biomolecules in a pistil. Therefore, CPEs were employed to investigate if the pollen tube growth stimulants from cut pistil tissues are diffusible in an in vitro pollen growth assay. This assay involved three steps: collection of CPEs, delivery of the exudates to pollen grains, and recording pollen germination and growth response. Using this assay, CPE obtained from 15 pistils (FIG. 1F) was observed to stimulate pollen germination (93% germination with CPE compared to 42% with liquid pollen growth medium; n=30 assays; Table 1) and growth of pollen tubes (320.25 μm long near a pistil compared to 147.78 μm with liquid pollen growth medium; n=30 assays; Table 2).

Example 2

Pollen Tube Growth Stimulating Activity is Mediated by a Small Molecule

The ability for CPE to stimulate pollen germination and pollen tube growth indicated the presence of a soluble, diffusible stimulant from the pistil. This example shows that the active pistil factor is a small molecule distinguishable from flavonols such as kaempferol.

Methods

CPE was prepared and in vitro pollen growth assays performed as described in Example 1.

Statistical Analysis:

The experiments described in Tables 1 and 2 were analyzed as a randomized complete block design with independent in vitro assays (n) as blocks and various treatments of the exudates as treatments. Mean germination percentages for each assay were used as primary data for analysis of germination percentage. Shapiro-Wilk statistics (Shapiro, and Wilk, Biometrika, 52:591-611, 1965) were calculated for germination percentage and pollen tube length within experiments to confirm that samples could be assumed to be from normally distributed populations. This was done using PROC UNIVARIATE in SAS/STAT Version 9.1 of the SAS System for Windows (Copyright® 2002-2003 SAS Institute Inc., Cary, N.C., USA.). Based on these statistics, pollen germination percentage was arcsine-transformed before analysis, and pollen tube length was analyzed without transformation. These variables were subjected to mixed-model analysis of variance with block considered a random effect, and treatment considered a fixed effect. Data were used from in vitro assays where all treatments in a comparison were included. Analysis was done using PROC MIXED in SAS/STAT, and least-squares means are reported. Pairwise comparisons (two-sided) of least-squares means were accomplished using the PDIFF option within PROC MIXED. Untransformed values are reported in all cases and statistical significance was assigned at ($P \leq 0.05$) in all cases.

Results

Physical Characterization of CPE

The physical characterization of the pollen growth activity of CPE is summarized in Tables 1 and 2. Size exclusion filtration of CPE into >3 kDa and <3 kDa fractions, followed by assaying stimulation of pollen germination and pollen tube growth indicated that pollen stimulating activities were present in the <3 kDa fraction. The ability of CPE to stimulate pollen germination and pollen tube growth was also heat stable and resistant to proteinase K and glycosidase F treatments, suggesting that the active component of CPE is not a protein or glycoprotein. Moreover, unlike small peptides and amino acids, the pollen stimulating activities were stable in base treatment and readily soluble in methanol. Resistance to base treatment also suggests that the activity is unlikely to be mediated by small oligosaccharides. Lastly, the active component of CPE could not be extracted with organic solvent such as ethyl acetate, making it likely that the pollen stimulating factor is not hydrophobic. This finding is consistent with our previous finding that these activities are freely diffusible in pollen growth medium. Taken together, these observations indicate that the pollen stimulating factor in CPE is a small molecule.

TABLE 1

Pollen germination activity in *Arabidopsis* cut pistil exudates

| Treatment | Fraction pollen germinated | Germination percentage (%) | n | Least squares means | P values |
|---|---|---|---|---|---|
| Cut pistil | 1009/1161 | 86.40 ± 4.59 | 7 | 86.68 | <0.0001* |
| Cut stem | 635/1178 | 54.55 ± 5.93 | 7 | 54.56 | |
| CPE | 2782/3554 | 78.35 ± 5.94 | 30 | 78.68 | — |
| PGM | 1446/3759 | 37.42 ± 10.94 | 30 | 37.18 | <0.0001* |
| chs CPE (tt4-020483) | 389/499 | 77.96 ± 6.09 | 5 | 78.22 | 0.7765 (NS) |
| chs CPE (tt4-2YY6) | 427/538 | 79.15 ± 5.74 | 5 | 79.41 | 0.4714 (NS) |
| Heat-treated CPE | 692/915 | 75.62 ± 8.45 | 6 | 76.63 | 0.396 (NS) |
| >30 kDa CPE | 277/798 | 35.08 ± 7.50 | 5 | 34.94 | 0.0015* |
| <30 kDa CPE | 576/803 | 71.34 ± 10.21 | 5 | 71.87 | 0.2428 (NS) |
| >3 kDa CPE | 183/531 | 34.67 ± 3.39 | 5 | 34.63 | <0.0001* |
| <3 kDa CPE | 373/473 | 78.70 ± 5.40 | 5 | 78.90 | 0.2176 (NS) |
| CPE + ProteinaseK | 451/583 | 77.22 ± 3.80 | 5 | 77.31 | 0.3781 (NS) |
| PGM + ProteinaseK | 177/576 | 30.74 ± 3.69 | 5 | 30.72 | <0.0001* |
| CPE + GlycosidaseF | 505/635 | 79.40 ± 7.67 | 5 | 79.87 | 0.2519 (NS) |
| PGM + GlycosidaseF | 306/658 | 45.56 ± 10.96 | 5 | 45.56 | 0.0029* |
| CPE + Acid | 461/595 | 77.49 ± 6.67 | 6 | 77.79 | 0.1965 (NS) |
| CPE + Base | 505/597 | 84.74 ± 7.33 | 6 | 85.26 | 0.1424 (NS) |
| CPE insoluble in MeOH | 210/555 | 37.90 ± 5.12 | 5 | 37.84 | <0.0001* |
| CPE soluble in MeOH | 447/557 | 80.08 ± 3.86 | 5 | 80.20 | 0.014 (NS) |
| CPE insoluble in EtOAc | 454/590 | 76.90 ± 7.49 | 6 | 77.29 | 0.2119 (NS) |
| CPE soluble in EtOAc | 201/580 | 34.81 ± 4.81 | 6 | 34.75 | <0.0001* |

CPE = Cut pistil exudates from 15 pistils collected in liquid pollen growth medium (PGM);
n = number of independent in vitro assays and germination rate of ≧80 pollen were measured in each assay;
P value, statistical analysis of separation between least square means of cut pistil and cut stem or between indicated treatment and CPE;
*P values < 0.05 were considered to be statistically significant;
NS, not significant if P value was >0.05;
chs CPE, CPE collected from indicated mutant alleles of CHALCONE SYNTHASE.

TABLE 2

Pollen tube growth activity in *Arabidopsis* cut pistil exudates

| Treatment | PT Length ± s.d. (mm) | n | Least squares means | P Values |
|---|---|---|---|---|
| Cut pistil | 381.98 ± 133.34 | 7 | 384.25 | <0.0001* |
| Cut stem | 180.54 ± 87.40 | 7 | 184.62 | |
| CPE | 317.03 ± 99.56 | 30 | 320.25 | — |
| PGM | 146.61 ± 68.55 | 30 | 147.78 | <0.0001* |
| chs CPE (tt4-020483) | 339.22 ± 81.35 | 5 | 339.19 | 0.2219 (NS) |
| chs CPE (tt4-2YY6) | 352.41 ± 93.86 | 5 | 352.34 | 0.4618 (NS) |
| Heat-treated CPE | 279.57 ± 89.14 | 6 | 289.1 | 0.0008* |
| >30 kDa CPE | 166.60 ± 81.57 | 5 | 168.72 | <0.0001* |
| <30 kDa CPE | 267.07 ± 93.94 | 5 | 270.9 | 0.4843 (NS) |
| >3 kDa CPE | 128.46 ± 60.28 | 5 | 128.59 | <0.0001* |
| <3 kDa CPE | 351.14 ± 68.53 | 5 | 350.64 | 0.5789 (NS) |
| CPE + ProteinaseK | 308.18 ± 116.18 | 5 | 308.01 | <0.0001* |
| PGM + ProteinaseK | 149.23 ± 75.52 | 5 | 148.82 | <0.0001* |
| CPE + GlycosidaseF | 275.24 ± 88.16 | 5 | 277.36 | 0.4839 (NS) |
| PGM + GlycosidaseF | 126.93 ± 81.01 | 5 | 133.14 | <0.0001* |
| CPE + Acid | 332.71 ± 80.93 | 4 | 322.78 | 0.930 (NS) |
| CPE + Base | 330.22 ± 57.50 | 6 | 330.17 | 0.0687 (NS) |
| CPE insoluble in MeOH | 128.38 ± 59.84 | 5 | 128.18 | <0.0251* |
| CPE soluble in MeOH | 338.09 ± 94.81 | 5 | 337.94 | 0.0008* |

TABLE 2-continued

Pollen tube growth activity in *Arabidopsis* cut pistil exudates

| Treatment | PT Length ± s.d. (mm) | n | Least squares means | P Values |
|---|---|---|---|---|
| CPE insoluble in EtOAc | 320.82 ± 68.74 | 6 | 320.74 | 0.0008* |
| CPE soluble in EtOAc | 121.17 ± 45.96 | 6 | 121.37 | <0.0001* |

CPE = Cut pistil exudates from 15 pistils collected in liquid pollen growth medium (PGM);
n = number of independent in vitro assays and germination rate of at least 50 pollen were measured in each assay;
P value, statistical analysis of separation between least square means of cut pistil and cut stem or between indicated treatment and CPE.
*P values < 0.05 were considered to be statistically significant.
NS, not significant if P value was >0.05;
chs CPE, CPE collected indicated mutant alleles of CHALCONE SYNTHASE.

Pollen Stimulating Factor of CPE is Likely Not a Flavonol

Flavonoids are known to function as plant developmental regulators including during pollen germination (Taylor and Grotewold, *Curr Opin Plant Biol*, 8:317-323, 2005). *Petunia* stigmatic extracts contain flavonols, especially kaempferol, that were shown to be capable of inducing pollen germination (Mo et al., *PNAS*, 89:7213-7217, 1992). Consistent with these observations, loss of maize and *Petunia* chalcone synthase (chs), the first enzyme of flavonoid biosynthesis, resulted in white pollen that was incapable of germinating, growing and fertilizing ovules (Id.). These studies raised the possibility that the pollen stimulating factor from *Arabidopsis* pistils could either be kaempferol or a closely-related flavonol.

Several lines of evidence, however, indicated that kaempferol is unlikely to mediate the pollen stimulation activities from *Arabidopsis* described here. First, kaempferol and related flavonols are highly soluble in ethyl acetate (Han et al., *Phytomedicine*, 14:338-343, 2007). In contrast, the active component of CPE was insoluble in ethyl acetate (Table 1). Second, it has been reported that an *Arabidopsis* chalcone synthase (chs) null mutant that is nearly devoid of all flavonols is 85% fertile and displays no in vivo pollen tube growth aberrations (Ylstra et al., *Plant Mol Biol*, 32:1155-1158, 1996); though another group reported a slight reduction in in vitro germination % of mutant pollen (Kim et al., *J Plant Biol*, 39:273-278, 1996). Third, CPE from two *Arabidopsis* chalcone synthase null mutants (tt4-2yy6 and tt4-SALK_020583) was tested for each of the pollen stimulating activities. As shown in Tables 1 and 2, CPE from both chs mutants stimulated both pollen activities to similar levels as that of CPE from wild type plants. Thus, it is highly unlikely that the pollen tube stimulant in *Arabidopsis* is a flavonol.

Example 3

Fractionation of CPE and Identification of the Pollen Tube Growth Stimulation Activity Physical characterization of the pollen stimulating factor of CPE indicated that the active factor was a small, non-proteinaceous molecule that is distinguishable from flavonoids. This example shows the fractionation of CPE and the determination of the chemical formula of the pollen stimulating factor.

Methods

Pistil Extract Preparation:

Pistil extracts were prepared by grinding 1000 pistils in liquid nitrogen. To this preparation, four mL of pollen growth medium without sucrose were added and additional grinding was performed. Following centrifugation, supernatant was extracted with two volumes of ethyl acetate. The soluble phase was again extracted with two volumes of ethyl acetate and the extraction was repeated two more times. Ultimately, the ethylacetate insoluble phase was air dried for several hours and resuspended in two mL of methanol. The methanol soluble fraction was then used either directly in the pollen germination bioassay or separated by liquid chromatography. Typically, extract volume equivalent to ~36 pistils or ~72 pistils were used in a small or large column respectively.

Liquid Chromatography:

Analytes were separated via HPLC, using Paradigm MS4B (multi-dimensional separations module) (Michrom BioResources, Inc., Auburn, Calif.) equipped with VYDAC 218TP51, 5 µm, 1.0×250 mm column (Grace Davison Discovery Sciences, Deerfield, Ill., USA). The mobile phases 0.01% TFA in acetonitrile (A) and 0.01% TFA in $H_2O$ (B) were delivered at a flow rate of 0.05 mL/min at the following gradient: 5% A (0-5 min), from 5 to 100% A (5-35 minutes), 100% A (35-40 minutes), from 100 to 5% A (40-45 minutes), 5% A (45-50 minutes). The volume of extract loaded on the column varied from 0.3 to 3 µL, it was brought up to 20 µL (injection volume) and the run duration was 50 minutes. UV detection was carried out via WellChrom spectrophotometer K-2501 (Knauer; Berlin, Germany) set at 190 nm and combined with a microbore flow cell. The fraction collector FC 203B (Gilson, Inc., Middleton, Wis.) was inline with MSB4. Chromatogram peak areas could be integrated using Michrom Paradigm version 2.0.0.7 software.

Liquid Chromatography Coupled Mass Spectrometric (LC-MS) Analysis:

MS analysis of fractions was performed on ABI/SCIEX 4000 QTRAP hybrid triple-quadrupole linear ion trap mass spectrometer (Applied Biosystems, Foster City, Calif.) with nanospray source with introduction of analytes via infusion at 2 µL/min by the syringe infusion pump Model 22 (Harvard apparatus, Holliston, Mass.). MS analysis of the synthesized compounds was performed with the TurbolonSpray source with the sample introduction via infusion. TurbolonSpray source was used for LCMS analysis of the whole extract with the sample introduction via MSB4.

The initial screening of samples was performed in the EMS mode (Enhanced MS). Detection of the compound of interest was performed via MRM scan type (Multiple Reaction Monitoring) in positive mode. As the compound of interest is being fragmented, the instrument detects m/z values of the precursor ion paired with the m/z values of the predetermined fragment ion derived from the corresponding precursor ions. MRM transition was as follows: m/z 201.40→137.40. While using the nanospray source, the following instrument parameters were used: source temperature, 150° C.; source voltage, 2100 V; collision energy (CE), 30 V; declustering potential (DP), 80 V; dwell time for all transitions, 200 msec; data acquisition duration, 5 min. While using the TurbolonSpray source the following instrument parameters were used: source temperature, 150° C.; source voltage, 5000 V; collision energy (CE), 25 V; declustering potential (DP), 20 V; data acquisition duration, 50 min.

Molecular Weight Determination and MS/MS Analysis Using FT-ICR:

The accurate mass determination for identification of the unknown compound and fragmentation (MS/MS) experiments were performed on a 9.4 T Bruker ApexQh Fourier-transform ion cyclotron resonance (FT-ICR) (Bruker Daltonics, Bellerica, Mass.). Electrospray ionization (ESI) was used to generated protonated molecules so that our measurements refer to the $[M+H]^+$ ion. For ESI, a water:acetonitrile 1:1 solution with 0.1% of formic acid was used with direct infusion from a syringe with a flow rate of 2.5 µL/min. For accurate mass measurements, the standard Agilent calibration mix spiked with triethyl, benzyl ammonium chloride (positive ion mass m/z 192.17467) and tributyl ammonium chloride (positive ion mass: m/z 242.28422) was used. The mass spectra were internally calibrated to achieve higher accuracy of the mass determination. Low energy collision induced dissociation was used in the quadrupole region of the instrument with argon as the collision gas (ev QCID with Ar) for fragmentation studies.

Results

To identify the pollen stimulating factor of CPE, HPLC was initially used to separate the CPE into fractions that were then tested for activity in the bioassays described in Examples 1 and 2. Preliminary results indicated that CPE from >600 pistils separated via HPLC may not be sufficient to identify the positive fraction. With a goal of scaling up the purification procedure, the pollen growth stimulating activity of ovules was examined. As shown in FIG. 1C, ovules also stimulated pollen germination and pollen tube growth (85.23%±3.51%, 401.60±18.16 μm tube length, FIG. 1C). In addition, like CPE, the OE stimulant is diffusible (OE, FIG. 1G), heat-stable, concentration-dependent, and behaved as a non-proteinaceous molecule (insensitive to Trypsin and Glycosidase F) with a molecular weight less than 3 kDa. Based on these results, whole pistils were used for the remainder of the purification procedures.

To exclude possible inhibitory factors from ground pistil tissues, the pollen stimulant activity was first partially purified by only retaining the ethyl acetate insoluble and methanol soluble fraction of the whole pistil extracts (FIG. 1H). The partially purified pistil extracts (from 200 pistils) were loaded on a reverse phase C18 column and the eluted fractions were combined, air-dried. The resultant pellet was resuspended in 500 μL methanol, air-dried, and resuspended in 50 μL liquid pollen growth medium and tested for stimulating activity in the in vitro assay described in Example 1. Significant stimulation of pollen germination and pollen tube growth was observed (62.47±4.95% pollen germination; tube length=189.47±13.12 μm) compared to blank sample control with no pollen germination after 3 hours. These results suggested that the pistil stimulant is compatible with the elution solvent.

Next, partially purified pistil extracts were separated into five minute fractions on a C18 column and tested for stimulating activity. It was found that the germination activity was present in the 15-20 minute and 20-25 minute fractions (FIGS. 2A, 2C). Further separation into 1-minute fractions demonstrated that 18-19 minute fraction contained the biologically active molecule (FIGS. 2B, 2D).

Figure 3:
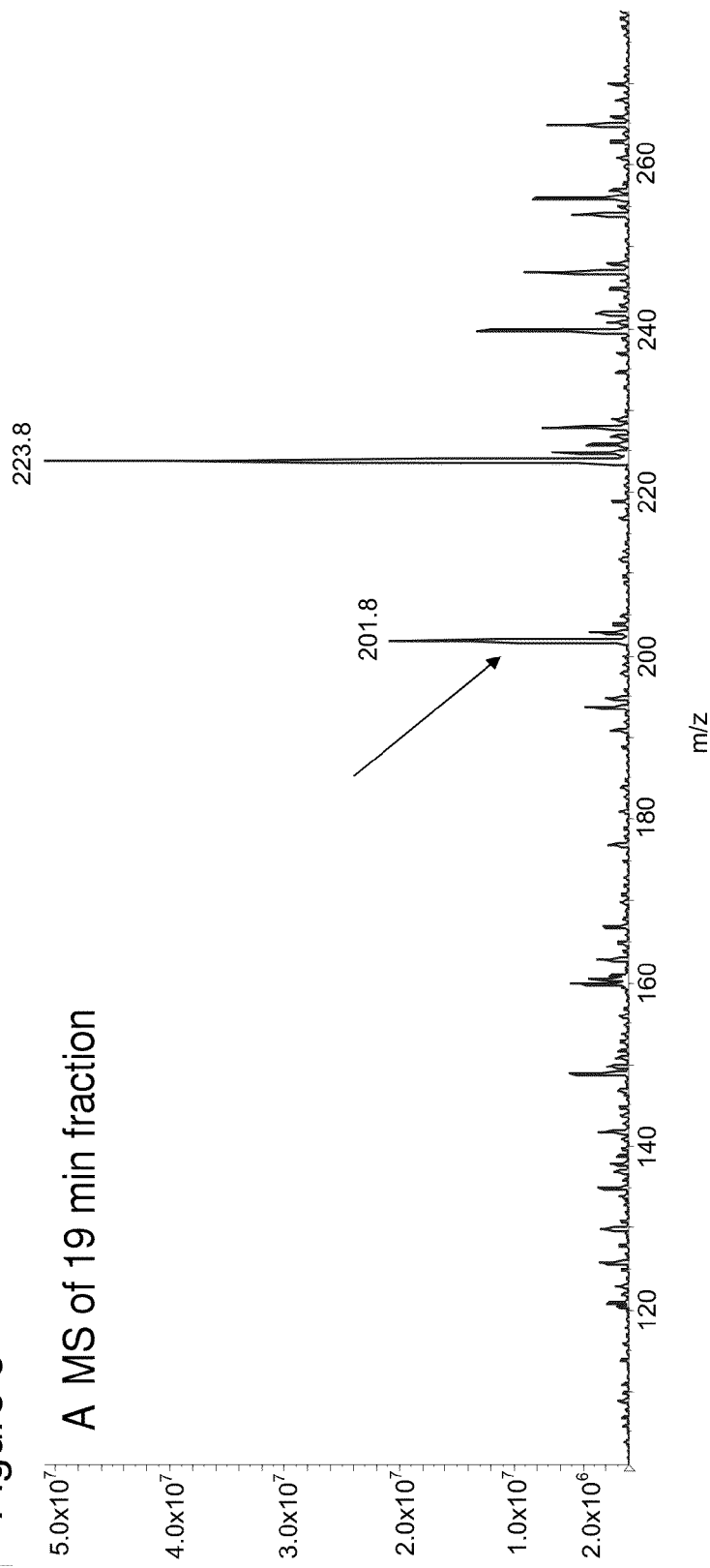
FIG. 3 shows the LC-MS spectra of the active (19 minute) (FIG. 3A) and inactive (8-10 minutes) (FIG. 3B) CPE fractions. The arrow in FIG. 3A indicates the active fraction-specific peak.
Figure 4A:
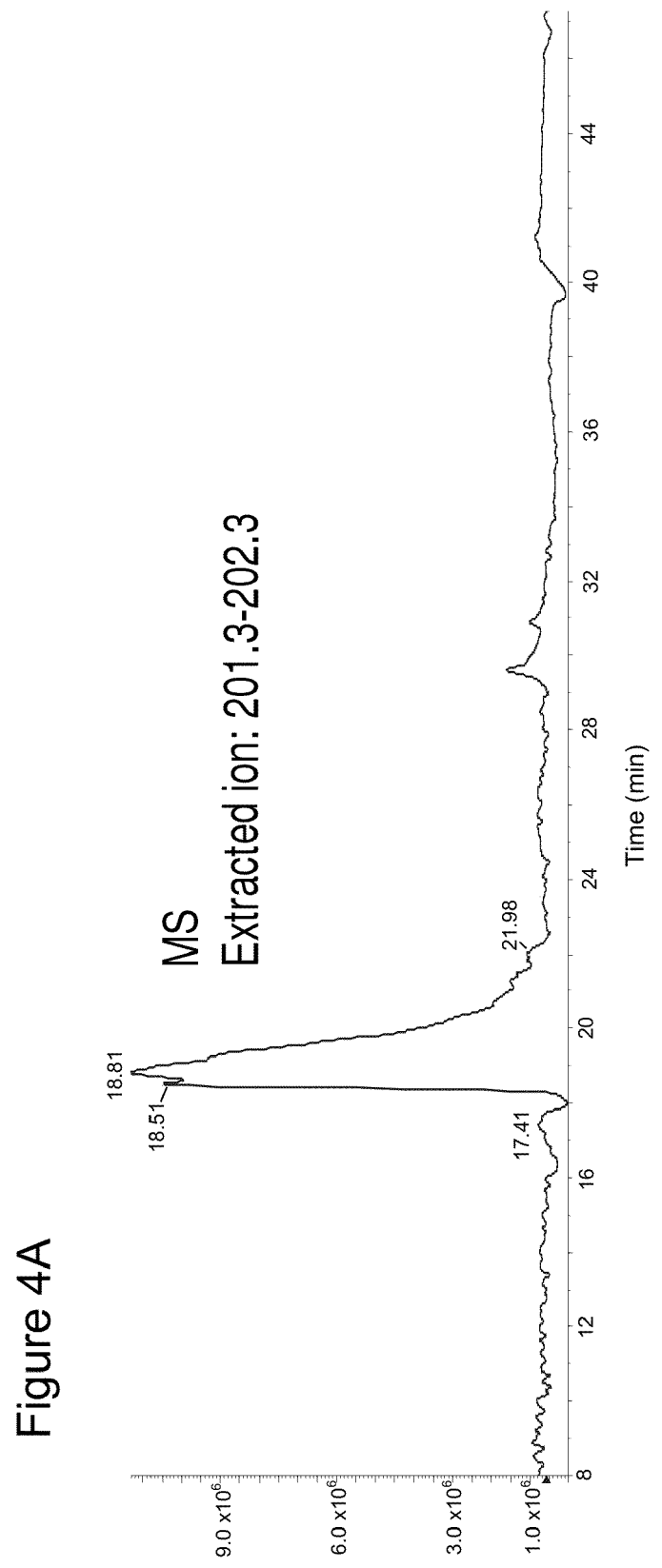
FIG. 4 shows MS (FIG. 4A) and MS/MS (FIG. 4B and FIG. 4C) spectra of the active CPE fraction.
Figure 4B:
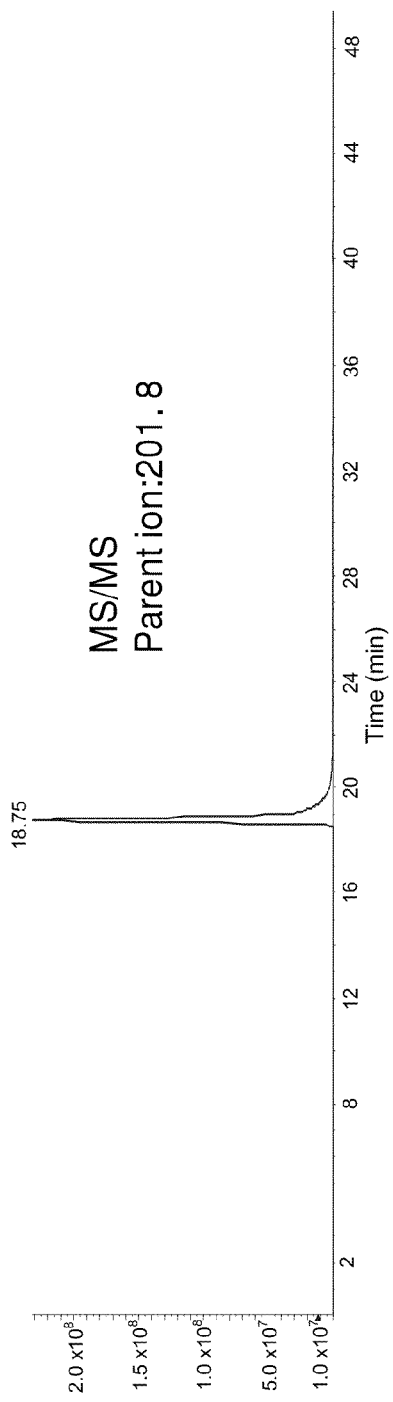
Figure 4C:
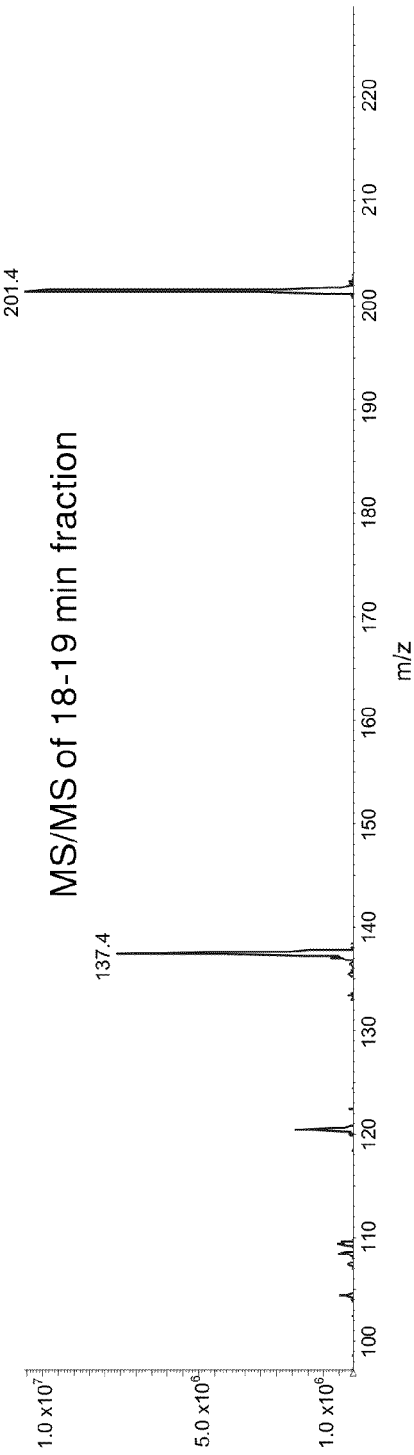

Using LC-MS, it was determined that a compound with a molecular mass of ~201 daltons is present only in the positive fraction (see the corresponding protonated molecule, [M+H]$^+$ at m/z 202 in FIG. 3A) and not in the inactive fractions (FIG. 3B and FIG. 4). MS/MS of the [M+H]$^+$ ion at m/z 202 identified a characteristic fragment at m/z 188. Using electrospray ionization (ESI) Fourier-transform ion cyclotron resonance (FT-ICR) measurements, the low-resolution mass spectral results were confirmed and the molecular weight/formula of this compound was accurately determined. ESI provided the protonated molecule [M+H]$^+$ in the positive ionization mode and the FT-ICR therefore allowed determination of the mass to charge ratio (m/z) of this ion with ultrahigh resolution and precision. The results showed that an ion with a mass of 202.12618 daltons is present only in the bioassay positive fraction and not in any other bioassay negative fractions (FIG. 5A). This measured mass of 202.12618 daltons corresponds to a chemical formula of $C_{10}H_{20}NSO$ for the [M+H]$^+$ ion (measured: 202.12618, calculated: 202.126011, 0.8 ppm error). Thus, it was possible to determine the chemical formula for the neutral compound as $C_{10}H_{19}NSO$. The fragmentation of the [M+H]$^+$ ion also demonstrated that a $CH_3SOH$ molecule is lost from the ion leading to a fragment at m/z 188, which is in agreement with the chemical formula and also with the low-resolution LC-MS results.

Example 4

Synthesis and Activity of Pollen Stimulating Compounds

Fractionation of the pollen stimulating factor of pistils identified an active compound with a formula of $C_{10}H_{20}NSO$. However, it was not possible to obtain sufficient material for NMR characterization of the corresponding compound. This example describes the synthesis and characterization of compounds sharing the identified formula but having varying structures, and the identification of two compounds able to stimulate pollen germination and pollen tube growth.

Methods

Preparation of Synthetic 202 m/z Compounds:

The N-methyl sulfinamides of the dialkyl or cyclic amines were prepared by a modification of the method of Piggotta and Karuso (*Tetrahedron Letters*, 48:7452-7455, 2007), where triethylamine as used as the base to trap the by-product hydrogen chloride and to prepare the free base from the hydrochloride salt. Reaction of a solution of the secondary amines in a solvent such as dichloromethane and triethylamine at 0° C. with methylsulfinylchloride for two hours affords the product sulfinamides in 70-79% yield after purification by flash chromatography. Methane sulfinyl chloride was prepared by the method of Youn and Herrmann (*Tetrahedron Letters*, 27:1493-1494, 1986). The characterization data ($^1H$ and $^{13}C$ NMR and mass spectra) were consistent with proposed structures. Detailed preparation procedures of each of the four compounds tested are provided below:

1. 1-Methylsulfinyldecahydroquinoline (Compound A)

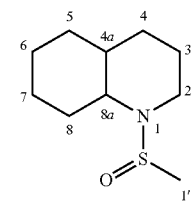

A solution of decahydroquinoline (1.07 g, 7.68 mmol) in anhydrous dichloromethane (10 mL) was cooled to −15° C. The reaction mixture was treated with triethylamine (1.07 mL, 7.68 mmol) and methanesulfinyl chloride (800 mg, 8.11 mmol). After 1 hour, the reaction mixture was placed in a −40° C. freezer overnight. The reaction mixture was warmed to room temperature and treated with 5% aq. $NaHCO_3$ (10 mL) and additional dichloromethane (10 mL) and was separated. The organic layer was washed with 3% aq. HCl (1×20 mL), 5% aq. $NaHCO_3$ (2×20 mL), water (1×20 mL), dried ($MgSO_4$) and concentrated in vacuo. Flash chromatography ($SiO_2$, ethyl acetate eluant) afforded the product as a yellow oil (1.2 g, 77%): $^1$H NMR (CDCl$_3$, 600 MHz, δ) 3.41-2.70 (m, 4H), 2.52 (s, 1.3H, C1'-H), 2.51 (s, 0.4H, C1'-H), 2.49 (s, 1.3H, C1'-H), 1.75-1.26 (m, 12H); $^{13}$C NMR (CDCl$_3$, 125 MHz, δ) 54.2, 49.2, 48.3, 47.8, 43.2, 42.6, 42.3, 41.6, 41.5, 41.4, 41.6, 41.5, 41.4, 39.0, 38.9, 38.84, 38.77, 35.6, 35.4, 34.0, 33.9, 33.1, 32.6, 32.5, 30.1, 30.0, 26.0, 25.7, 25.6; ESIMS m/z 224.2 (4, MNa$^+$), 204.1 (5, $^{32}$S), 203.0 (13, $^{13}$C), 202.0 (base, MH$^+$); ESIHRMS m/z 202.1260 (calculated for C$_{10}$H$_{20}$NOS 202.1260).

2. 2-Methylsulfinyldecahydroisoquinoline (Compound B)

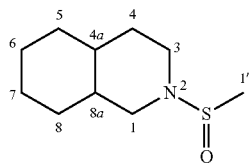

A solution of decahydroisoquinoline (1.16 g, 8.33 mmol) and triethylamine (1.1 g, 10.9 mmol) in anhydrous dichloromethane (20 mL) was cooled in a dry ice/acetone bath. The reaction mixture was treated with methanesulfinyl chloride (1.1 g, 11.2 mmol) dropwise. The reaction mixture was stirred and warmed to room temperature. After 5 h, the reaction mixture was filtered through Celite®. The filtrate was collected, washed with water (1×20 mL), dried (MgSO$_4$) and concentrated in vacuo. Flash chromatography (SiO$_2$, ethyl acetate eluant) afforded the product as a white solid (1.0 g, 60%) mp XX ° C.: $^1$H NMR (CDCl$_3$, 600 MHz, δ) 3.39-3.34 (m, 1H, C1-H), 3.22-3.15 (m, 1H, C1-H), 2.90-2.85 and 2.73-2.68 (m, 1H, C-3H), 2.51-2.47 (m, 0.5H, C3-H) and 2.34 (t, 0.5H, J=11 Hz, C3-H), 2.51 (s, 1.5H, C1'-H) and 2.50 (s, 1.5H, C1'-H), 1.69-1.49 (m, 5H), 1.29-1.13 (m, 4H), 0.96-0.86 (m, 3H); $^{13}$C NMR (CDCl$_3$, 125 MHz, δ) 54.3, 49.3, 48.4, 43.3, 42.4, 41.7, 41.6, 41.5, 39.14, 39.05, 38.95, 38.88, 33.2, 32.7, 32.6, 30.2, 30.1, 26.13, 26.12, 25.76, 25.71; ESIMS m/z 204.1 (5, $^{32}$S), 203.0 (13, $^{13}$C), 202.0 (base, MH$^+$); ESIHRMS m/z 202.1260 (calculated for C$_{10}$H$_{20}$NOS 202.1260).

The decahydroisoquinoline and decahydroquinoline are available commercially only as mixtures of cis and trans isomers at the 4a, 8a ring fusion. For each reactant amine, the methanesulfinylation reaction creates a mixture of diastereomers through the stereoisomers generated by the sulfoxo bond of the sulfonamide. This mixture can obscure the NMR data assignments.

3. 3,3-Dimethyl-1-(thiomorpholino)butan-1-one

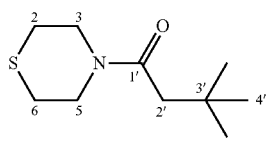

A solution of thiomorpholine (1.0 g, 9.69 mmol), triethylamine (2.0 mL, 14.3 mmol) and 4-dimethylaminopyridine (10 mg) in anhydrous tetrahydrofuran (12 mL) was cooled in an ice bath. The reaction mixture was treated with 3,3-dimethylbutanoyl chloride (1.7 mL, 12.1 mmol) dropwise. The reaction solution was stirred and allowed to warm to room temperature. After 2 hours, the reaction mixture was diluted with diethyl ether (20 mL) and was filtered through a CELITE® filter. The pad was washed with diethyl ether (1×10 mL). The combined wash and filtrate were collected and concentrated in vacuo. The resultant oil was taken into ether (30 mL), washed with 5% aq. HCl (2×30 mL), water (1×30 mL), 5% aq. NaHCO$_3$ (3×30 mL), dried (MgSO$_4$) and concentrated in vacuo. The resultant oil was crystallized from hexanes to afford white plates (1.0 g, 51%) mp XX ° C. $^1$H NMR (CDCl$_3$, 500 MHz, δ) 3.87 (br t, 2H, J=5.0 Hz, C-3 or C-5H), 3.75 (br t, 2H, J=5.0 Hz, C-5 or C-3H), 2.58 (br t, 4H, J=5.0 Hz, C-2 and C-6H), 2.22 (s, 2H, C-2'H), 1.02 (s, 9H, C-4'H); $^{13}$C NMR (CDCl$_3$, 125 MHz, δ) 170.3 (C-1'), 49.2 (C-3'), 44.7 (C-3 or C-5), 44.0 (C-5 or C-3), 31.4 (C-2'), 30.0 (C-4'), 27.8 (C-2 or C-6), 27.5 (C-6 or C-2); ESIMS m/z 203 (13), 202.1 (base, MH$^+$), 104 (43). ESIHRMS m/z 202.1257 (calculated for C$_{10}$H$_{20}$NOS 202.1260).

Reaction of dimethyl disulfide, sulfuryl chloride and acetic acid followed by distillation afforded the product as a colorless oil: $^1$H NMR (CDCl$_3$, 600 MHz, δ) 3.33 (s, 3H); GCMS m/z (rel abun) 100 (CH$_3$$^{37}$ClOS, 12), 98 (CH$_3$$^{35}$ClOS, 36), 63 (base), 48 (25).

4. 10-(Methylsulfinyl)-10-azabicyclo[4.3.1]decane

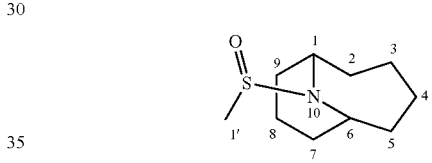

A mixture of 10-azabicyclo[4.3.1]decane hydrochloride (10 mg, 0.057 mmol) in anhydrous diethyl ether (1 mL) was cooled in an ice bath. The reaction mixture was treated with triethylamine (0.1 mL, 0.72 mmol) and methanesulfinyl chloride (10 mg, 0.1 mmol). The reaction vial was sealed and placed in a −40° C. freezer overnight. The reaction mixture was warmed to room temp, diluted with ether (2 mL), washed with water (2×1 mL), sat. aq. KCl (1×2 mL), dried (MgSO$_4$) and concentrated in vacuo. Flash chromatography (SiO$_2$, ethyl acetate eluant) afforded the product as an oil (8.1 mg, 71%): $^1$H NMR (CDCl$_3$, 600 MHz, δ) 4.02 (br quin, 1H, J=4 Hz, C1- or C9-H), 3.84 (br quin, 1H, J=4 Hz, C1- or C9-H), 2.55 (s, 3H, C1'H), 1.88-1.72 (m, 5H), 1.65-1.48 (m, 9H); ESIMS m/z 224.1 (89, MNa$^+$), 202.1 (base, MH$^+$); ESIHRMS m/z 202.1260 (calculated for C$_{10}$H$_{20}$NOS 202.1260).

Pollen Tube Germination and Growth Bioassay with Synthesized m/z 202 Compounds:

Synthetic compounds (two microliters=two milligrams) were directly dissolved in methanol, air dried and resuspended in 50 μL of liquid pollen growth medium. The dissolved compounds were applied in the hole in solid pollen growth medium plates. Pollen was placed within a 2 mm radius from the hole in which compounds were dispensed, and plates were incubated at 22° C. in a chamber for 3 hours before imaging as described in Example 1.

Results

Figure 6:
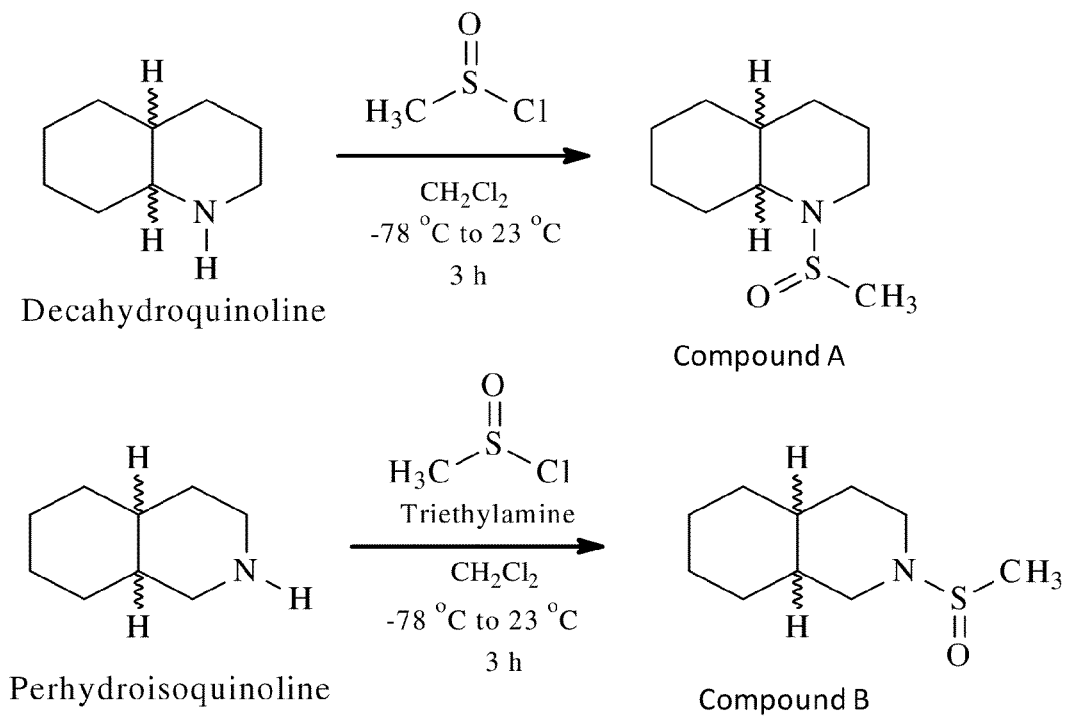
FIG. 6 is a schematic drawing of the sulfinylation of quinoline compounds to produce Compounds A and B.

Based on the MS/MS and FT-ICR results, which identified the formula of the m/z 202 [M+H]$^+$ ion, two possible corresponding structures were initially predicted. (FIG. 6). Using commercially available precursors, compounds having these structures (Compounds A and B) were then synthesized as described in the methods (and shown schematically in FIG. 6).

Figure 7:
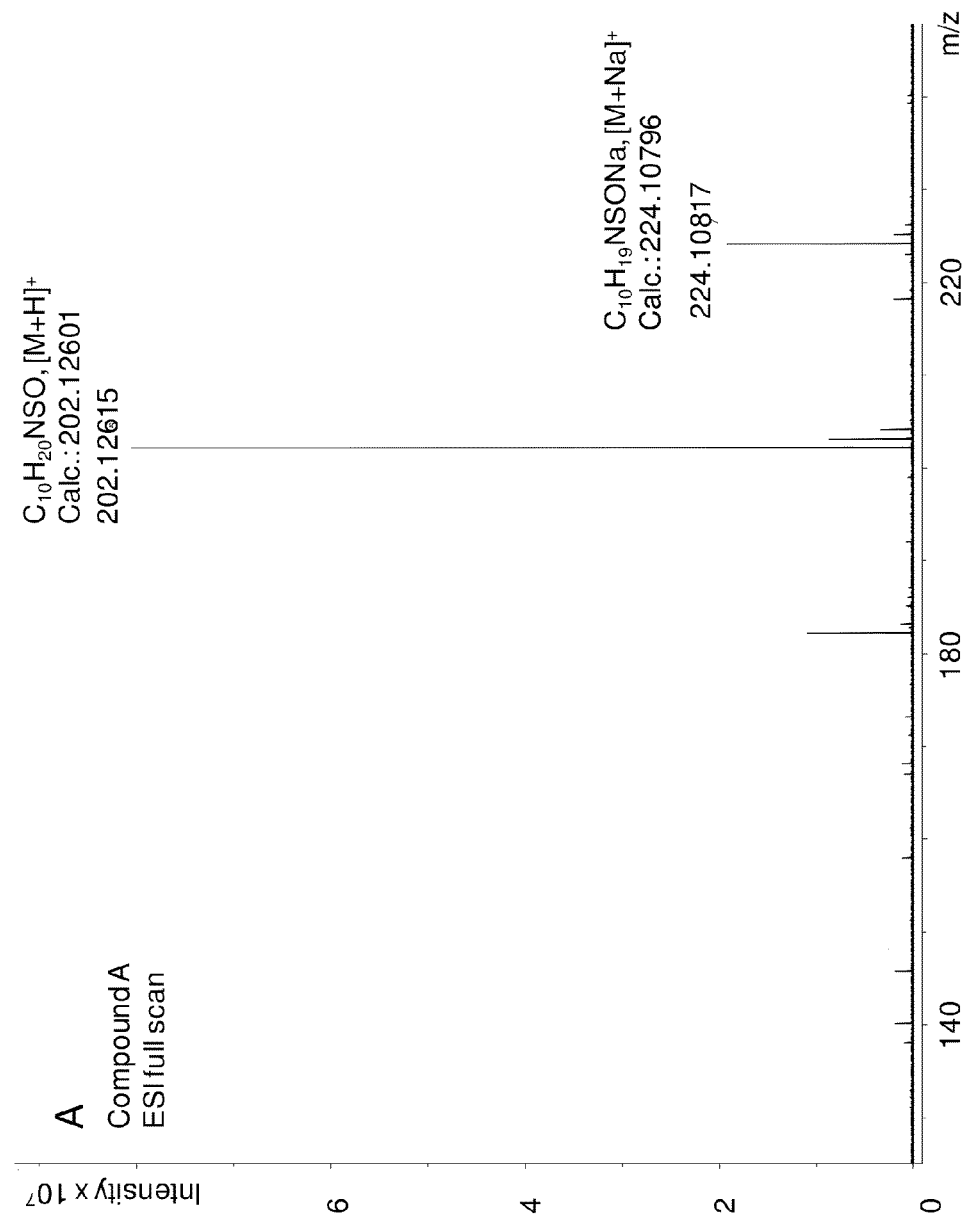
FIG. 7A is a FT-ICR spectrum of Compound A.
FIG. 7B is a MS/MS fragmentation spectrum of Compound A.
Figure 7:
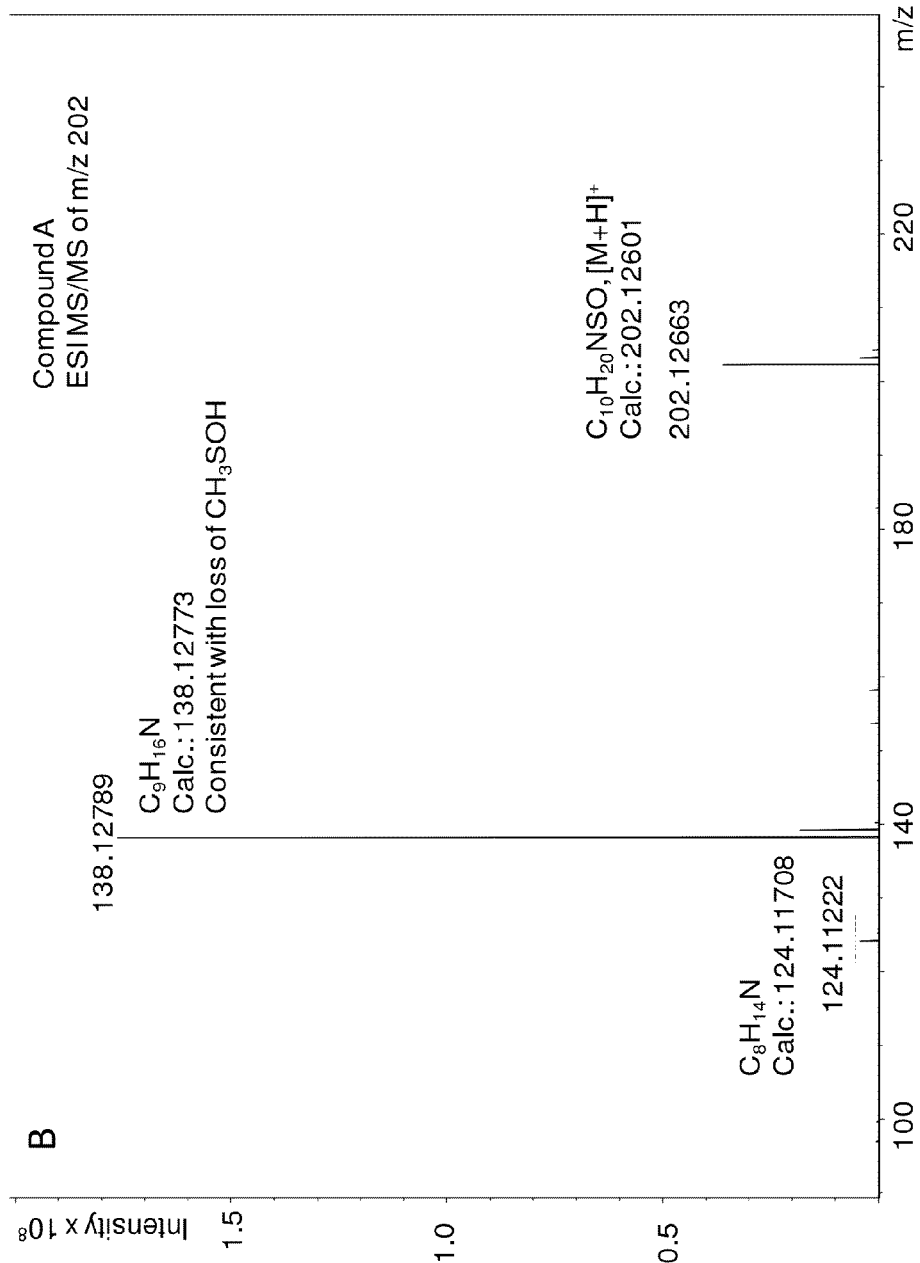
Figure 8:
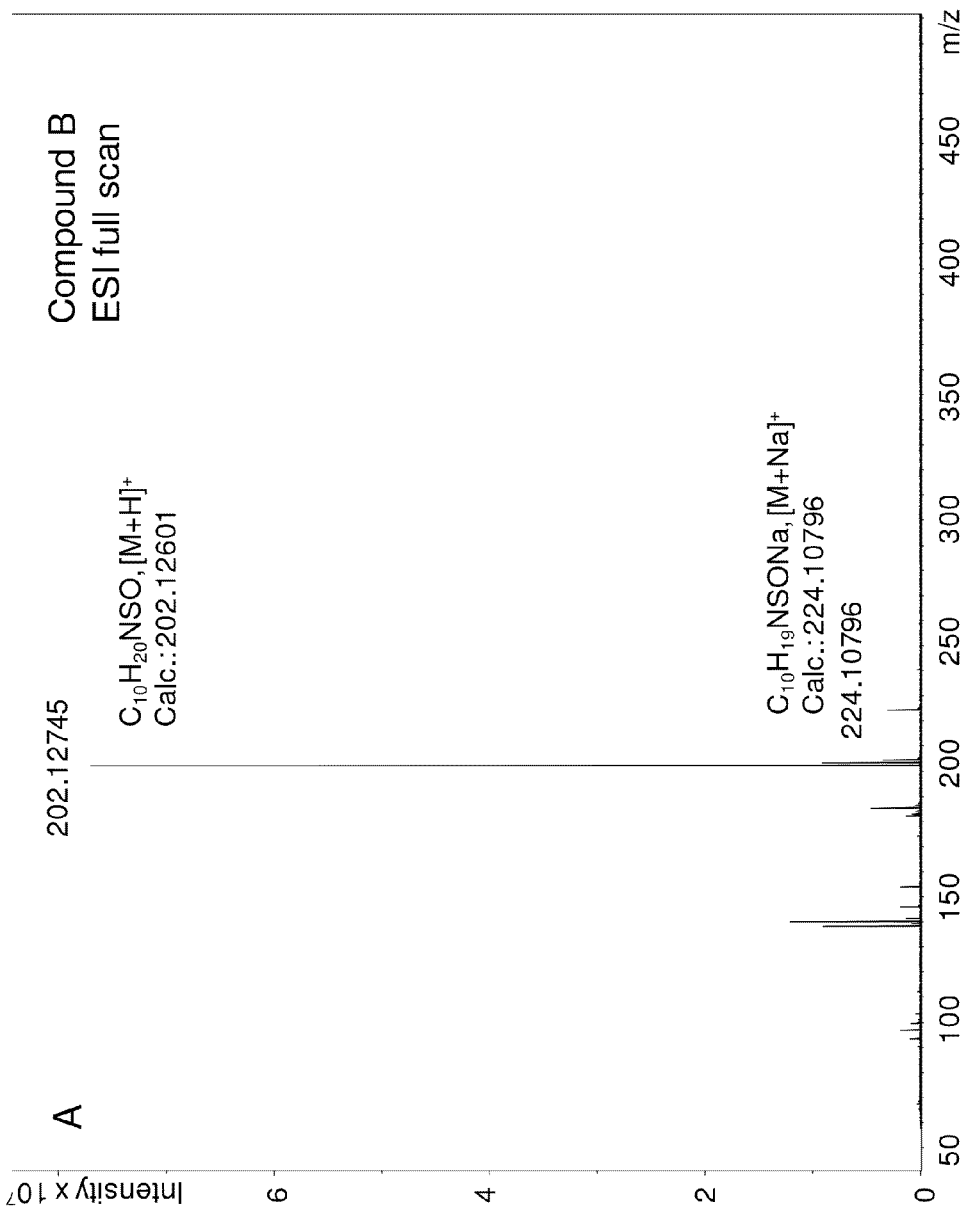
FIG. 8A is a FT-ICR spectrum of Compound B.
FIG. 8B is a MS/MS fragmentation spectrum of Compound B.
Figure 8:
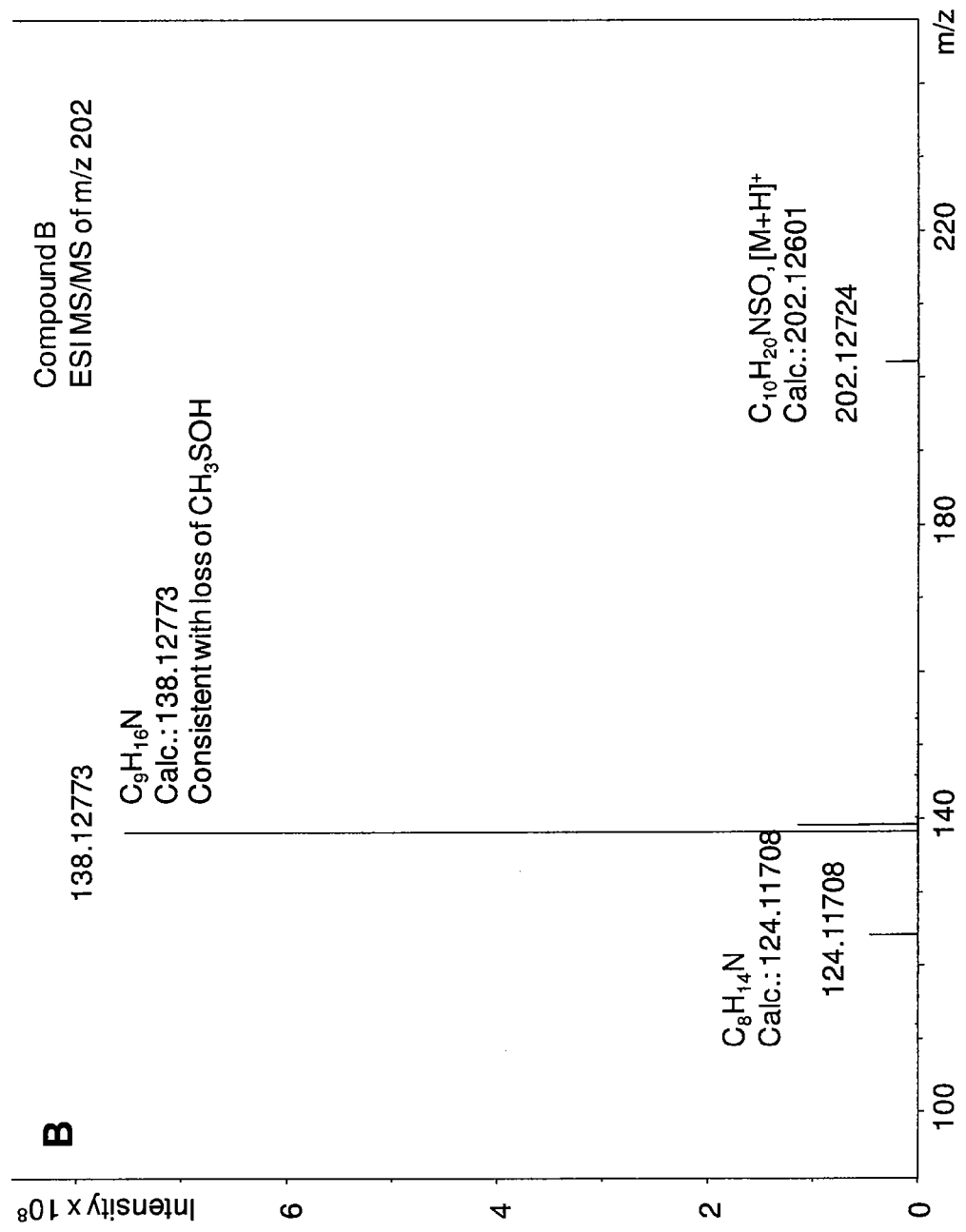

The purity and molecular weight of the synthesized compounds were determined by ESI FT-ICR, and established that the synthesized compounds shared similar chemical properties as that of the m/z 202 ion (FIGS. 7A and 8A). Similar to m/z 202.12618, the loss of CH$_3$SOH group was also observed upon MS/MS fragmentation (FIGS. 7B and 8B), suggesting that synthesized compounds shared similar chemical structures as that of the bioactive compound fractionated from the pistil extracts.

Figure 9:
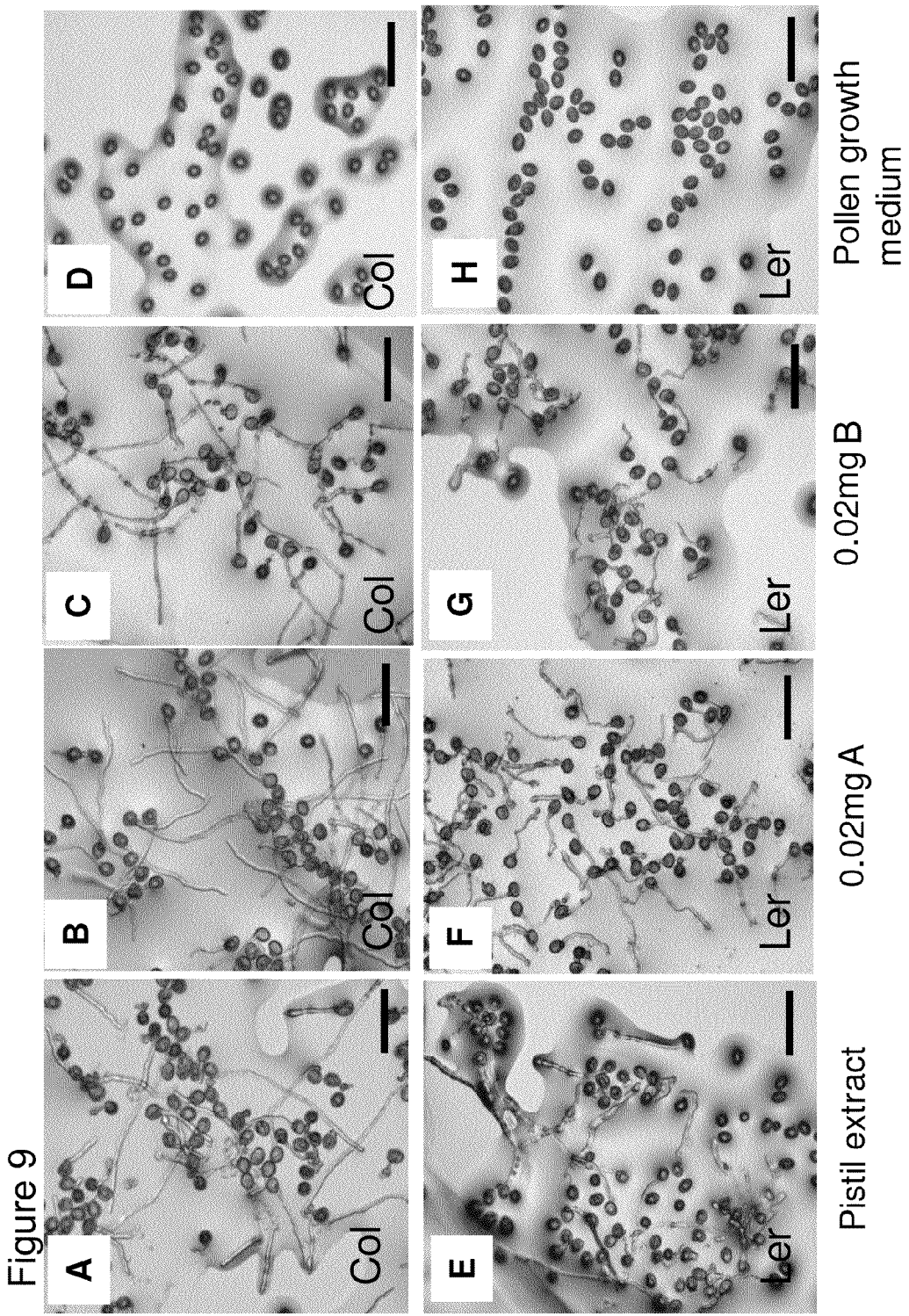
FIGS. 9A-9H are a series of photomicrographs comparing the stimulation of *Arabidopsis* Columbia (top row) and Landsberg (bottom row) pollen in the in vitro growth assay in response to the following factors: CPE (FIGS. 9A and 9E); 0.2 mg of Compound A (FIGS. 9B and 9F); 0.2 mg of Compound B (FIGS. 9C and 9G); and PGM (FIGS. 9D and 9H). The black bar in each figure represents 50 micrometers.

To assess the pollen stimulating activity of the synthesized compounds, different concentrations of the two synthesized compounds were utilized in the in vitro pollen stimulation assay as described in Example 1. Assessment of pollen germination and pollen tube growth in the presence of synthesized compounds showed that both synthesized compounds stimulated pollen germination and pollen tube growth (FIGS. 9B-9C, 9F-9G) more than no compound control (FIG. 9D, 9H). This effect was specific to the synthesized compounds, as neither of the quinoline precursors of Compound A or B stimulated pollen germination or pollen tube growth. Additionally, similar to cut pistil tissues (FIG. 10A, 9B), cut pistil exudates and ovule exudates (FIG. 10C, 9D), the synthesized compounds' stimulation activities were also concentration dependent (FIGS. 10E-9H). These results established that synthesized m/z 202 compounds with the chemical formula of C$_{10}$H$_{19}$NSO contained pollen germination and growth stimulation activities.

Compounds A and B also enhanced the rate of pollen germination. Using the optimal concentration of compound for pollen tube stimulation (0.02 mg compound dispensed into 50 μL of pollen growth medium) pollen tube growth were time lapse imaged for a duration of greater than 12 hours. Results from these experiments showed that *Arabidopsis* pollen initiated germination approximately two hours earlier in the presence of the two synthesized compounds compared to no compound controls (FIGS. 11A, 11B). Interestingly, compounds A and B exhibited strain-dependent differences in their stimulating abilities. For example, pollen from the *Arabidopsis* Columbia strain showed robust growth by 3 hours after exposure to the compounds, while pollen from the Landsberg strain required at least 5 hours before exhibiting germination and pollen tube growth. Similarly, while Columbia pollen grew to a similar extent when exposed to either compound A or B, Landsberg pollen exhibited compound-specific growth responses. For example, Landsberg pollen grew about 130 μm longer in the presence of compound A compared to compound B (FIG. 11B).

Figure 12:
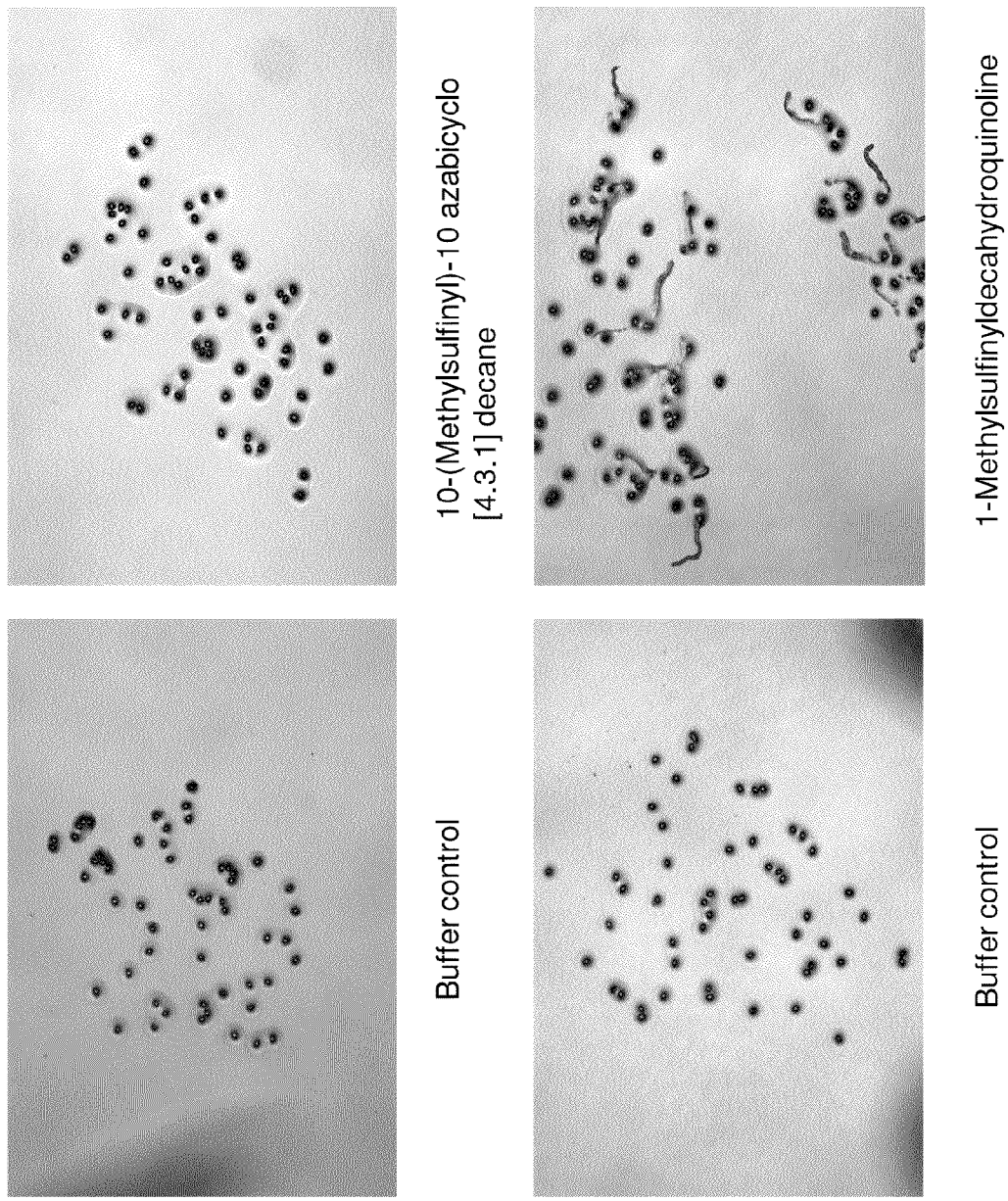
FIG. 12 is a series of photomicrographs comparing the effect of 10-(Methylsulfinyl)-10-azabicyclo[4.3.1]decane and 1-Methylsulfinyldecahydroquinoline (Compound A) on *Arabidopsis* pollen germination and pollen tube growth.
Figure 13:
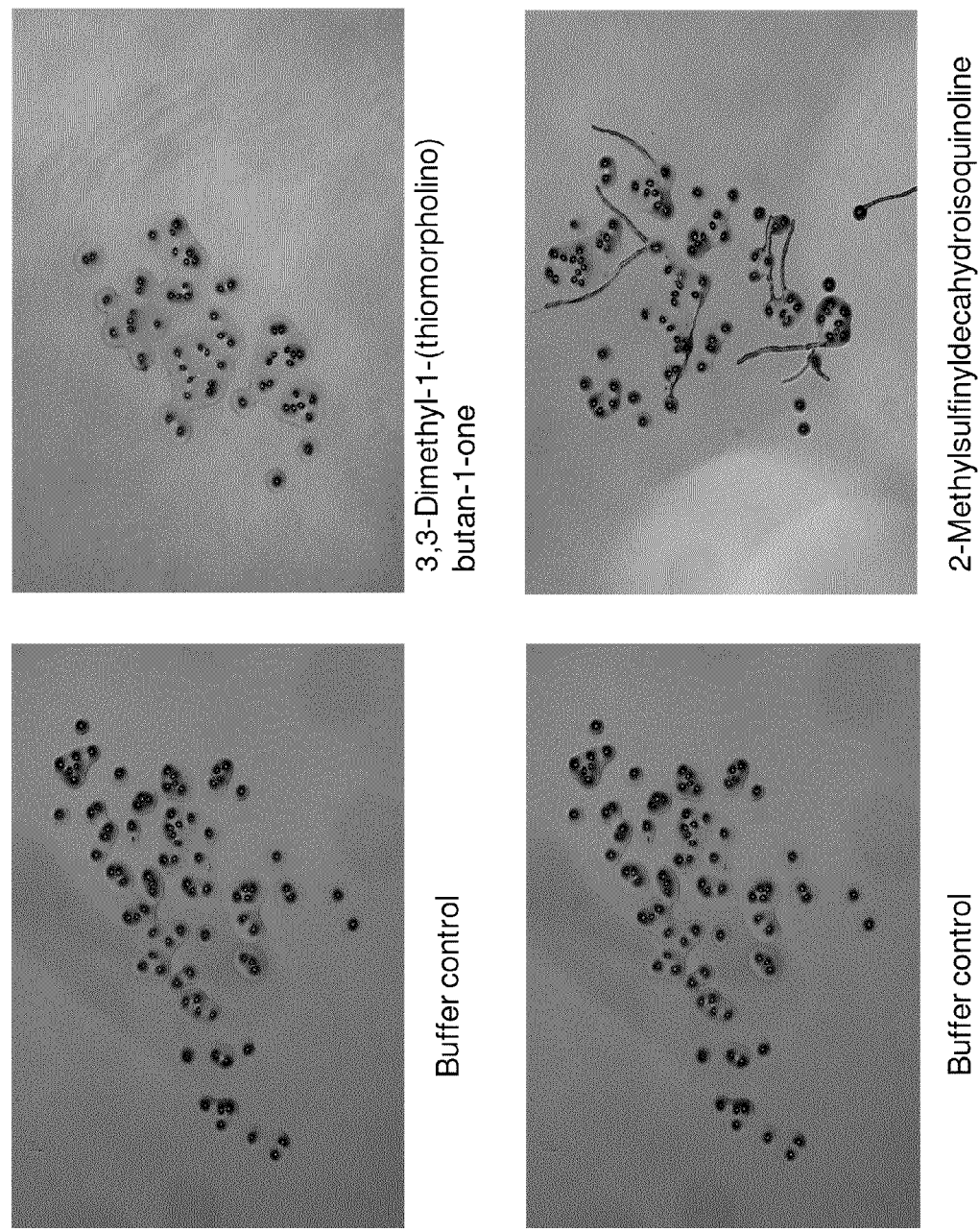
FIG. 13 is a series of photomicrographs comparing the effects of 3,3-Dimethyl-1-(thiomorpholino)butan-1-one and 2-Methylsulfinyldecahydroisoquinoline (Compound B) on *Arabidopsis* pollen germination and pollen tube growth.

To evaluate the specificity of pollen stimulation activity in quinoline compounds, we synthesized two other m/z 202 compounds that have the same formula but different structure than that of quinoline-based Compounds A and B. As shown in FIGS. 12 and 13, neither of the non-quinoline based compounds stimulated pollen germination similar to Compound A or B. These results suggest that the pollen stimulation activity of quinolines is specific and that any compound of chemical formula of C$_{10}$H$_{19}$NSO is not sufficient to stimulate pollen germination.

Example 5

Stimulation of Pollen Germination and Pollen Tube Growth In Vivo

The identification and synthesis of compounds capable of stimulating pollen germination and pollen tube growth in vitro immediately suggests in vivo applications for such compounds. This example illustrates the stimulation of pollen germination and pollen tube growth on a plant using the identified pollen growth stimulants.

The stimulation of pollen germination in vivo may be achieved by applying an effective amount of one or both Compound A or Compound B, or functional derivative thereof, to a plant, such as *Arabidopsis thaliana*, ecotype Columbia, or another plant that is sufficiently evolutionarily related to *Arabidopsis*, such as a member of family Brassicaceae. The pollen growth stimulant can be applied in any formulation such as described herein and by any method of applying a compound to the flower of a plant. For example, an effective amount of Compound A can be sprayed onto any given number of plants in an area after blossoms open and pistils are exposed. As a control, the same number of plants can be grown under similar conditions, except for the addition of Compound A. Following pollination of test and control plants, stimulation of pollen germination and pollen tube growth will be indicated by an increased seed yield from those plants exposed to Compound A compared to the seed yield from those plants that were not exposed to Compound A.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated pollen-growth stimulant, comprising at least one compound having a structural formula as follows:

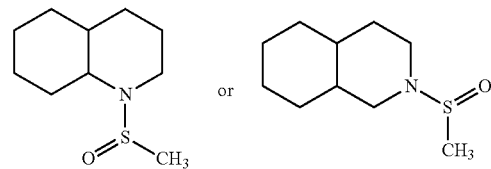

or mixtures thereof.

2. A formulation, comprising the isolated pollen growth stimulant of claim 1 and at least one of a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, and a pesticide.

3. The formulation of claim 2, further comprising pollen.

4. The formulation of claim 3, wherein the pollen is from a plant of family Brassicaceae.

5. The formulation of claim 4, wherein the plant is selected from the group consisting of species of *Arabidopsis, Olimarabidopsis, Capsella, Sisimbrium*, and *Brassica*, and hybrids thereof.

6. A composition, comprising the isolated pollen growth stimulant of claim 1 and pollen.

7. The composition of claim 6, wherein the pollen is from a plant of family Brassicaceae.

8. The composition of claim 7, wherein the plant is selected from the group consisting of species of *Arabidopsis, Olimarabidopsis, Capsella, Sisimbrium*, and *Brassica*, and hybrids thereof.

* * * * *